United States Patent [19]
Sarver et al.

[11] Patent Number: 5,847,804
[45] Date of Patent: Dec. 8, 1998

[54] MULTI-CAMERA CORNEAL ANALYSIS SYSTEM

[75] Inventors: Edwin J. Sarver, Merritt Island, Fla.; Henry D'Souza, Cypress, Tex.

[73] Assignee: Eyesys Technologies, Inc., Houston, Tex.

[21] Appl. No.: 638,875

[22] Filed: Apr. 25, 1996

Related U.S. Application Data

[63] Continuation of Ser. No. 330,979, Oct. 28, 1994, abandoned.

[51] Int. Cl.$^6$ .................................................. A61B 3/14
[52] U.S. Cl. ........................................ 351/206; 351/212
[58] Field of Search .................................. 351/211, 206, 351/212, 221, 247

[56] References Cited

U.S. PATENT DOCUMENTS

| | | | |
|---|---|---|---|
| 3,169,459 | 2/1965 | Friedberg et al. | 95/18 |
| 4,420,228 | 12/1983 | Humphrey | 351/212 |
| 4,597,648 | 7/1986 | Feldon et al. | 351/212 |
| 4,662,730 | 5/1987 | Outwater et al. | 351/212 |
| 4,685,140 | 8/1987 | Mount, II | 382/6 |
| 4,710,003 | 12/1987 | Masuda et al. | 351/212 |
| 4,859,051 | 8/1989 | Fukuma et al. | 351/211 |
| 4,863,260 | 9/1989 | Gersten et al. | 351/212 |
| 4,978,213 | 12/1990 | El Hage | 351/212 |
| 4,998,819 | 3/1991 | Labinger et al. | 351/212 |
| 5,110,200 | 5/1992 | Snook et al. | 351/212 |
| 5,212,506 | 5/1993 | Yoshimatsu et al. | 351/246 |
| 5,345,281 | 9/1994 | Taboada et al. | 351/209 |
| 5,382,989 | 1/1995 | Uomori et al. | 351/209 |

FOREIGN PATENT DOCUMENTS

| | | | |
|---|---|---|---|
| 0 589 857 A1 | 3/1994 | European Pat. Off. | A61B 3/107 |

OTHER PUBLICATIONS

Koch, et al., "The Corneal EyeSys System: Accuracy Analysis and Reproducibility of First–Generation Prototype", *Refractive & Corneal Surgery,* 5:424–429 (Nov./Dec. 1989).

Bibby, et al., "Corneal Topography–Its Measurement Description Application", Reprinted from Contact Lens Forum (Nov./Dec. 1976–Jan. 1977).

Bogan, et al., "Classification of Normal Corneal Topography Based On Computer–Assisted Videokeratopgraphy", *Archive of Ophthalmology,* 108:945–949 (Jul. 1990).

Rowsey, et al., "Corneal Topography, Corneascope", *Archive of Ophthalmology,* 99:1093–1100 (Jun. 1981).

Rowsey, et al., "Prospective Evaluation of Radial Keratotomy, Photokeratorscope Corneal Topography", *Ophthalmology,* 95(3):322–334 (Mar. 1988).

Henslee, et al., "New corneal Shapes In Keratorefractive Surgery", *Ophthalmology,* 90(3):245–250 (Mar. 1983).

Gormley, et al., "Corneal Modeling", *Cornea,* 7(1):30–35 (1988).

"Holographic Process Offers Best Potential for Real–time Modeling/Corneal Imaging", *Oscular Surgery News,* 6(4):16 & 18 (Feb. 15, 1988).

(List continued on next page.)

*Primary Examiner*—William L. Sikes
*Assistant Examiner*—James A. Dudek
*Attorney, Agent, or Firm*—Arnold, White & Durkee

[57] ABSTRACT

The invention relates to the art of corneal topography. More specifically, the invention provides many methods and apparatuses for advancing the ease and accuracy of corneal topography. In addition to a front-view camera, one embodiment provides a side (temporal) view camera for viewing the cornea or other reflective surface. The side-view camera may capture a true image of the cornea as well as a reflected placido pattern. The information contained in these images provides capability to automatically find the apex, location of the limbus, vertical profile and curvature out to the limbus. These abilities lead to improved methods for auto-calibration and autopositioning as well as other advantages in the field of corneal mapping.

32 Claims, 5 Drawing Sheets

OTHER PUBLICATIONS

"Three–Dimensional Ultrasonic Imaging of the Cornea, A Proposed Technique Would Generate Pictures of Curved Surfaces", *NASA Tech Briefs,* NASA's Jet Propulsion Laboratory, Pasadena, California, p. 99 (Sep. 1988).

"Real–Time Keratometer" *Nasa Tech. Briefs,* NASA's Jet Propulsion Laboratory, Pasadena, California, pp. 55–56 (Mar. 1988).

Villasenor, et al., "Corneal Topography and Refractive Surgery", *Cornea,* 2:323–331 (1983).

Doss et al., "Method for Calculation of Corneal Profile and Power Distribution", submitted to the Archives of Ophthalmology, pp. 1–14 & four pgs. drawings. (Dec. 1978).

Cotran, et al., "An Adaptation of the Topcon Slit Lamp for Photokeratoscopy", *CLAO Journal,* 13(5):277–279 (Sep. 1987).

Klyce, Stephen, "Corneal Topography Graphically Rendered By New System," *Ocular Surgery News,* pp. 28–29 (Apr. 1, 1987).

Klyce, Stephen D., "Computer–Assisted Corneal Topography", *Investigative Opthalmology & Visual Science,* 13(12):1426–1435 (Dec. 1984).

Maguire, et al., "Graphic Presentation of Computer–Analyzed Keratoscope Photographs", *Arch. Ophthalmol.,* vol. 105, pp. 223–230 (Feb. 1987).

Brochure: "The Leading Edge In Eye Care", *Computer Graphics World,* (Mar. 1987).

The University of Houston–University Park Subgrant Under The Coordinating Board, Texas University & College System, subgrantor–Technitex, Inc., *Development of the Photo–Keratographs*–(Aug. 1, 1986–Jan. 31, 1987).

MULTI-CAMERA CORNEAL ANALYSIS SYSTEM

This application is a continuation of Ser. No. 08/330,979 filed Oct. 28, 1994, now abandoned.

1.0 BACKGROUND OF THE INVENTION

1.2 Glossary

Apex: The specification may refer to the "apex of the eye" or "apex of the cornea." Referring to a cross section of an eye in FIG. 1, Apex 101 is the outermost point of the cornea.

Reflecting surface: The specification may refer to a "reflecting surface." It is intended that the term indicate any surface of a unit under test that is suitable for reflecting light (visible or otherwise), such as a ball bearing, marble, or human cornea.

Horizontal Meridian: The horizontal meridian is the profile of the cornea along a line containing the apex and is horizontal with respect to the imaging camera.

Vertical Meridian: The vertical meridian is the profile of the cornea along a line containing the apex and is vertical with respect to the imaging camera.

Z-axis: Generally, the Z-axis refers to an axis in parallel with the optical axis.

Unit Under Test: The "unit under test" refers to a reflecting surface under examination by the topography system. A "unit under test" may be any reflecting surface such as an eye, calibration ball, ball bearing etc.

Keratometer: An instrument for determining the curvature shape of the corneal surface which generally uses a placido or other illuminated target that is centered around the patient's line of sight. The reflection of a placido or other illuminated target by the patient's cornea or by the tear film on the anterior surface of the cornea is subsequently analyzed to determine the surface contour of the eye.

1.1 The History And Background Of Corneal Modeling

A number of forms of eye surgery involve a consideration of corneal surface topography. In radial keratotomy, for example, a number of cuts are made into the cornea in order to change its curvature and correct refractive power so that images focus closer to the retina.

While ophthalmic surgery is often successfully performed, the results obtained have been subject to variation occasioned by the particular operating "style" of the individual surgeon which dictates the number, location and depth of incision. Elements of subjective judgment are paramount. It would be useful to provide a device that could assist the surgeon in more quantitatively assessing pre-operative and post-operative corneal contours.

The present system relates to improvements in the art of photokeratometry and more particularly to the use of multiple camera view in combination with digital image processing techniques to ascertain the radius of curvature, refractive power, vertical profile of the cornea, and location of the apex.

An initial development in keratometry came from Gullstrand in 1896. Gullstrand disclosed the foundation for the current technology but his apparatus had no provision to compensate for aberrations in the optical system other than limiting the photographic coverage of the cornea to a 4 mm area. As a result, multiple exposures and calculations were necessary to map the corneal surface.

Much of the modern technique was developed by Amsler in 1930 and embodied in his "Photo-Keratoscope" which also required measurement and calculation as a separate step to derive the corneal shape data.

A standard instrument which is in common use for central optical zone shape measurement is the Bausch and Lomb Keratometer. Several companies offer similar devices with similar principles of operation. In these devices a single Mire image is projected on a small central portion of the anterior surface of the cornea usually 3 mm in diameter. The user is required to operate several controls to bring the optically split Mire images reflected from the cornea simultaneously into focus and alignment. In addition, the operator manually records the data obtained at two perpendicular axes. Other instruments are also available, such as the Haag-Streit Javal Schiotz device which measures only one axis at a time, but is slightly easier to use and tends to be more accurate in practice than the Bausch and Lomb system. In addition there exists a photographic system made by International Diagnostic Instrument Limited under the trademark "CORNEASCOPE" (and a similar system made by Nidek in Japan), as well as autokeratometers by several manufacturers. The CORNEASCOPE produces instant photographs of the reflection of a placido disc and requires a second instrument separate from the camera assembly to analyze the data. This system is fairly accurate, but expensive and tedious to use. The autokeratometers all are believed to be limited to a single zone of approximately 3 mm diameter and, in cases where the magnitude of the astigmatism is low, are inaccurate in their assessment of axes of astigmatism. Also available are three computer-direct systems which use conventional image analysis algorithms in conjunction with a mini-computer. These are the Corneal Modeling System (CMS) introduce in 1987 by Computed Anatomy, Inc. of New York, N.Y. and the ECT-100, introduced into the market by Visioptic of Houston, Tex. and a system using light emitting diodes disposed in concentric rings built by Zeiss of Germany. The placido disc-photo technique is regarded by some as superior to the Bausch and Lomb Keratometer because of the much greater amount of corneal surface analyzed form the placido reflection as opposed to the MIRES of the Keratometer.

A number of patents have been issued that relate to keratometers. U.S. Pat. No. 3,797,921 proposes the use of a camera to record the placido reflection from a patients eye. From this photograph, the radius of surface curvature of the cornea is determined at several points and calculated using a complex computer system. The use of a ground glass focusing screen with the small aperture of the optical system and large linear magnification makes use difficult and requires a darkened room for operation.

U.S. Pat. No. 4,440,477 proposes a method and device for measuring the corneal surface, comprising a slit lamp for illuminating the corneal surface, a camera for recording the reflection from the corneal surface, and a processor to calculate the image distance and the radius of curvature of the eye. The operation of the processor evidently is not detailed in U.S. Pat. No. 4,440,477.

A more recent entry into the market is the "Corneal Modeling System" manufactured by Computed Anatomy Incorporated of New York which uses a light cone placido target in conjunction with a "frame grabber" to digitize and store for conventional image analysis the pictorial data. The placido is in cylindrical form and illuminated from one end. This cylindrical placido maintains a small aperture optical system creating a large depth of field of focus of the imaging system and, consequently, requires a sophisticated focus determining apparatus to assure accurate and reproducible image evaluation. This system is said to produce corneal thickness data using a scanning laser, as well as the surface contour, but is very expensive and does not readily lend itself to clinical applications which are increasingly cost driven.

The prior art systems generally rely on a front view of the cornea to provide all the expected data. In many respects, this limitation causes significant potential for error or impracticality. The current invention addresses many of the suggested problems by providing a side (temporal) view of the cornea in addition to the traditional front view.

1.3 Problems In The Prior Art

Most current placido based systems cannot provide a three space location of the apex because front-view-only systems operate using a 2-D virtual image. While using a 2-D virtual image, it may be impossible to determine the true Z-axis location of the apex and therefore a three space location of the apex may not be found. While certain laser aided systems have claimed some success in finding the apex, the process is believed to be simpler and faster using the placido based multi-camera system proposed by the current invention.

As with apex location, most current placido based systems technology apparently cannot provide true topography data because of the limitations of the front-view virtual image. However, like the apex situation, the invention addresses this problem by providing a side-view real image in which the true topography can found.

Another limitation in the prior art is the general inability to accurately profile the cornea. A front-view-only system suffers this limitation because there may be no way to accurately locate even a single point on the Z axis. The multi-camera system of the current invention addresses this limitation because a side-view camera is able to profile the Z axis.

In addition to the other limitations discussed, the front-view-only systems in the prior art may cause severe errors because geometrical phenomenon can result in an identical data collection for more than one eye shape. The current invention circumvents this problem by providing a second view to act as a checking mechanism.

Furthermore, the front-view-only systems of the prior art are difficult to use in that they inherently rely on the subjective skill of the operator for accurately positioning the equipment with respect to the eye. For even the most experienced operators, this manual positioning factor can cause serious repeatability problems. The current invention is not as susceptible to these problems because the ability to locate the apex allows a system design whereby the system may auto-calibrate and auto-position. Furthermore, prior art systems can be slow to calibrate and position. Therefore drying of the tear film may result and cause patient discomfort and distorted reflected data.

Lastly, the geometric constraints of single-view placido based systems can make it difficult or impossible to collect data as far out as the limbus. The current invention addresses this problem by using the side view to retrieve the data.

2.0 SUMMARY OF THE INVENTION

As discussed above, prior art corneal topography generally has attempted to assess the surface of the cornea using only a front view of the eye (generally along the optical axis). The invention seeks to improve upon the prior art by assessing corneal topography with a multi-camera corneal analysis system. Generally, this multi-camera system assesses topography in light of a front view as well as a side view that is substantially orthogonal to the front view. Either alone, or in combination with front-view data, side-view data can be used to achieve several beneficial results discussed herein.

In one embodiment, the invention includes a multi-camera corneal analysis system. The invention specifies the addition of a side-view camera subsystem 702. The side-view camera subsystem provides for capture of a corneal image from a vantage point substantially orthogonal to the standard front-view camera. The camera subsystem includes the necessary and conventional circuitry for digitizing a captured image. This particular embodiment envisions that the side-view camera will be rigidly affixed relative to the front-view camera. Of course, given its position, the side-view camera has an optical axis that is substantially orthogonal (75–105 degrees) to the optical axis of the front-view camera. The described embodiment also envisions a subsystem 407 to analyze the digitized images and generate an error signal. The contemplated error signal is defined by the locational displacement of the apex from either (1) a desired position for the apex or (2) a point on a predefined coordinate system. Of course, the coordinate system may be easily defined by any one optical axis or the intersection of any two. Lastly, the described embodiment envisions the visual display of periodically updated information.

Another embodiment of the invention includes a third camera (second side-view camera) mounted opposite the first side-view camera and substantially orthogonal to the front-view camera. The optical axes of the side view cameras may coincide, cross or exist in parallel.

Yet another embodiment of the invention uses a side view camera to receive images reflected off a reflecting surface. The source of the image may be a placido. One skilled in the art will recognize the many embodiments that may be created by combining the advantages of a side-view camera with the many other elements of the a corneal analysis system. For example, given the apex-finding capabilities of the multi-camera system, an embodiment may be constructed to determine the desired location of the apex and even automatically adjust the cameras to align with the apex.

Several methods are contemplated to take advantage of the usefulness of the side-view camera. One of the contemplated methods includes steps for finding the apex of a reflecting surface. In brief, an image is captured by a side view camera and the apex is located at the leading edge of the cornea's vertical profile. Furthermore, consistent with the envisioned system, the method may specify that an error signal is generated to represent the difference between an actual apex location and a desired apex location.

The invention also includes a method of finding radius of curvature using a side view camera. Essentially, the system of the invention is used to gather a table of data for reflecting surfaces having known radii of curvature, e.g., balls. Specifically, the table should contain data representing known radii of curvature versus measured distances between specified locations on a pattern reflected off the surfaces (balls). After the table is constructed, the same pattern-location to pattern-location measurements are made for a unit under test. The radius of curvature are then found by interpolation with the know radii and measured distances.

Another aspect of the invention is a method of locating a point on a limbus. The side-view camera is used to capture an image of the cornea. The limbus is then found as the transition between a homogeneous white region and a non-homogeneous region. Of course, this result may be achieved using digitized images and detecting the transition between energy regions.

Yet another embodiment of the current invention is a method of finding a profile of a reflecting surface. An image is captured from a side view camera and digitized. Once digitized, the image may be high-pass filtered. The profile is then found at a high to low energy transition.

3.0 BRIEF DESCRIPTION OF THE DRAWINGS

4.0 DETAILED DESCRIPTION OF THE INVENTION

4.1 A Multi-Camera Apparatus

Figure 3:
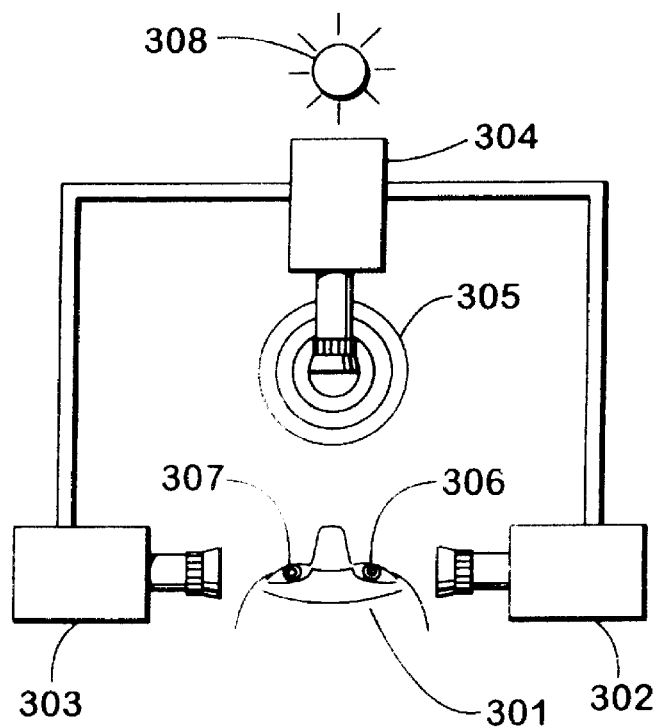
FIG. 3 is a three camera embodiment of the invention.

Referring to FIG. 3, a three camera embodiment of the invention is shown. Front view camera 304 has its optical axis generally aligned with the optical axis of the eye under exam 306 or 307. Of course, at any given time, front view camera 304 may be used for examining either left eye 307 or right eye 306, but not both. Side-view cameras 302 and 303 are each positioned substantially orthogonal to front view camera 304. Left-side-view camera 303 is used only for examining left eye 307 because human facial anatomy (usually a nose) substantially restricts visibility of right eye 306 from the vantage point of left-side-view camera 303. Of course, for the same reason, right-side-view camera 302 is only used for examining right eye 306. In one embodiment, left-side-view camera 303 and right-side-view camera 302 share a common optical axis.

Figure 5:
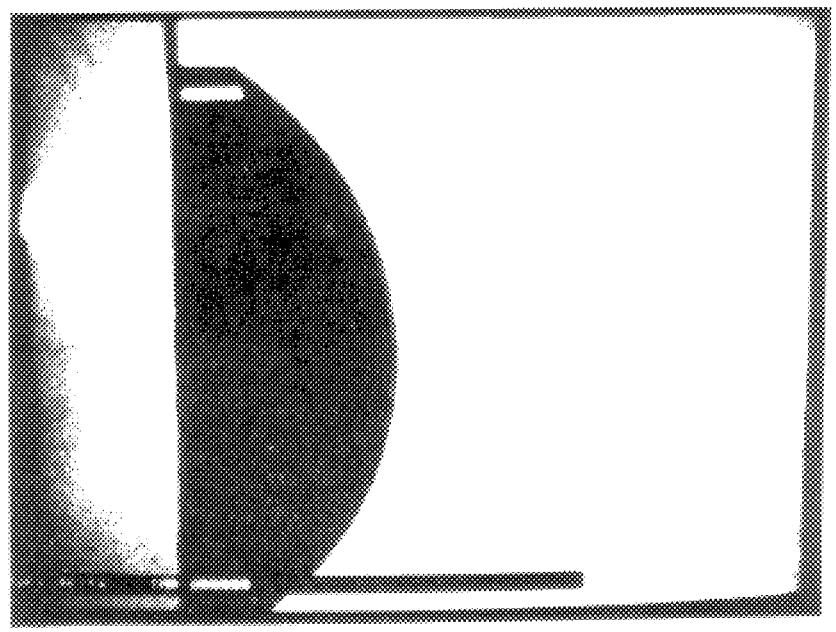
FIG. 5 is a graphic depiction of a processed profile of a sphere.
Figure 6:
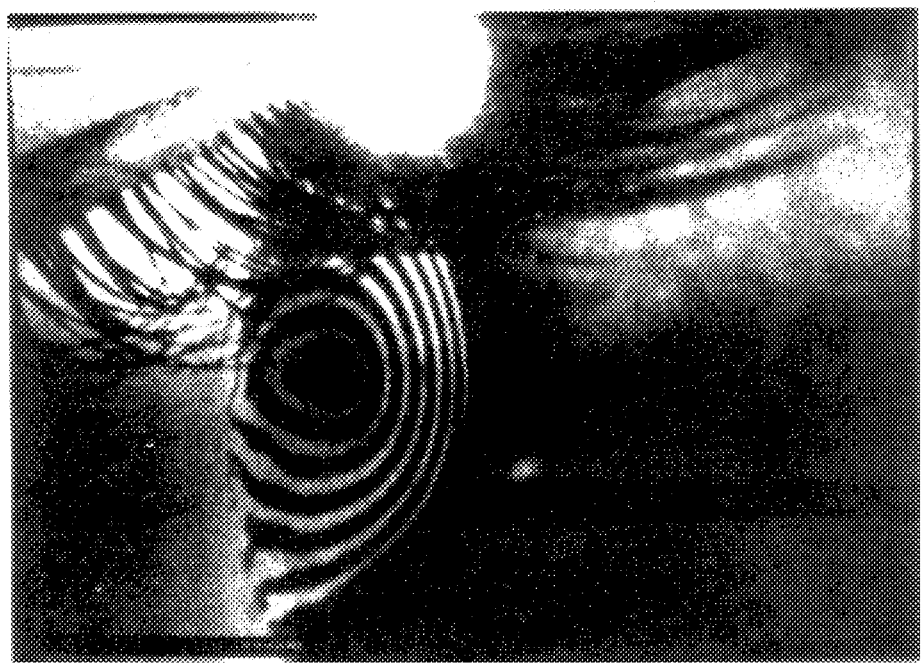
FIG. 6 is a graphic depiction of a processed profile of an optical sphere.

During a typical use of the invention, for example examining a right eye, a person under exam 301 will face placido 305 and generally align the optical axis of right eye 306 with the optical axis of front view camera 304. Light source 308 will cause the pattern from placido 305 to reflect off of right eye 306. The reflected pattern as well as a real image of the right eye 306 may be captured by front-view-camera 304 and right-view-camera 302. The corneal image captured by front-view-camera 304 is well known in the art and therefore not discussed further. However, the image captured by the right-side-view camera is not well known and provides two very useful data sources: (1) a true profile of the cornea; and (2) a view of the reflected placido rings on the temporal hemisphere. An example of this data is shown in FIG. 5 and FIG. 6. Specifically, a processed interpretation of a side-view image is shown in FIG. 6 (for a human eye) and FIG. 5 (for a sphere). Another typical use of the invention is, for example, examining the left eye 307. In this use, a person under exam 301 will face placido 305 and generally align the optical axis of left eye 307 with the optical axis of front view camera 304. The reflected pattern, real image and true profile of left eye 307 may then be captured by front-view-camera 304 and left-view-camera 303.

It will be apparent to those of ordinary skill having the benefit of this disclosure that the effect of a multi-camera system is to simultaneously achieve two views of a single eye (or cornea): a side view and a front view. It is contemplated that this effect can be achieved with fewer than three cameras. For example, two cameras may be oriented for use with one eye and then re-oriented for use with the other eye. Alternatively, one camera may be adapted with lenses or mirrors so that side and front views may be simultaneously received. Lastly, simultaneous views may be simulated by time sharing one camera with two or more views.

While no specific embodiment is envisioned, the invention also contemplates using a third view taken from the top or bottom vantage point. This third view may lead to even further accuracy in corneal topographic mapping by providing new information as well as verification information.

4.1.1 Orientation of views

Figure 4:
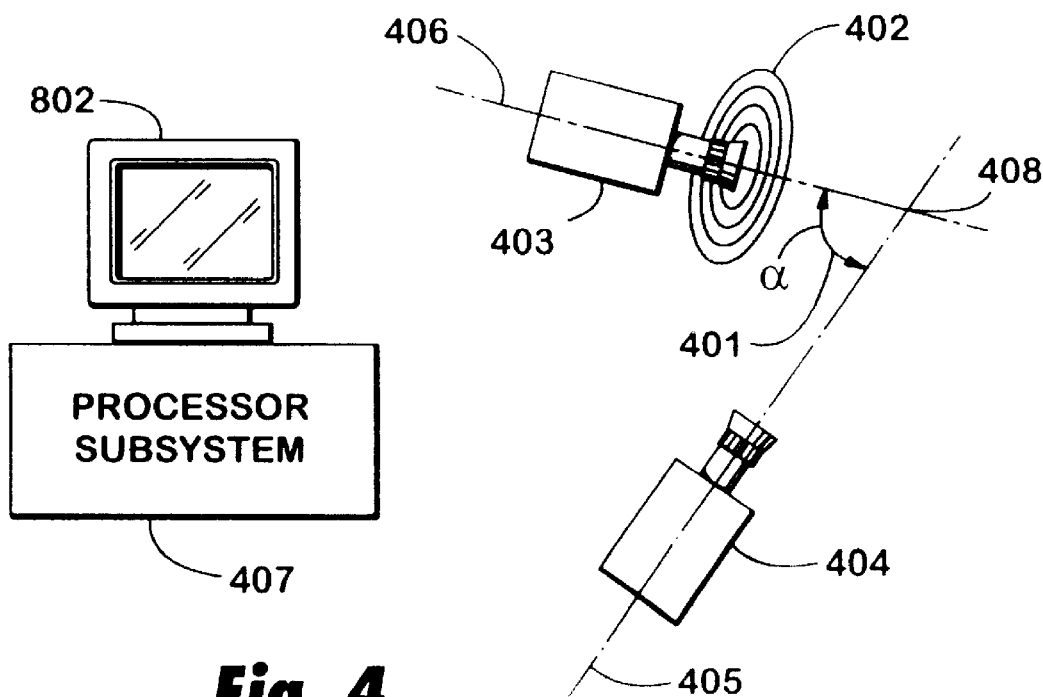
FIG. 4 is a two camera embodiment of the invention.

Referring now to FIG. 4, an abstract view of a multi-camera system is shown. Here, it can be seen that the optical axis 406 of front-view camera 403 is at angle $\alpha$ with the optical axis 405 of side-view camera 404. Any orientation of side-view camera 404 relative to front-view camera 403 may be used as long as the respective optical axes are substantially orthogonal to one and other; a maximum variation of $\alpha$ from 75 degrees to 105 degrees is preferred. However, it has been found that better performance may be achieved for $\alpha$ between 85 degrees and 95 degree. Furthermore, it has also been determined that $\alpha$ is optimum at 90 degrees.

While angle $\alpha$ is restricted as stated above, the relative orientation of side-camera 404 and front-camera 403 may be otherwise altered to maximize the view of the cornea. For example, some patients have facial structures that do not easily accommodate a side view of the cornea. In this instance, the corneal view may be improved by rotating side-view camera 404 about the optical axis of front-view camera 406.

4.1.2 Processor Subsystem

In order to increase efficiency and performance, a processor subsystem 407 is used to perform control and interface functions. Processor subsystem 407 initiates or performs all control functions and digital operations. Specifically, processor subsystem 407 is programmed to perform the functions necessary to receive meaningful data from the multi-camera system. For example, radius of curvature, position of the limbus, auto-calibration and error correction all benefit from computational activity in processor subsystem 407. Of course, the functions of processor subsystem 407 may be distributed across various devices or computers.

Figure 8:
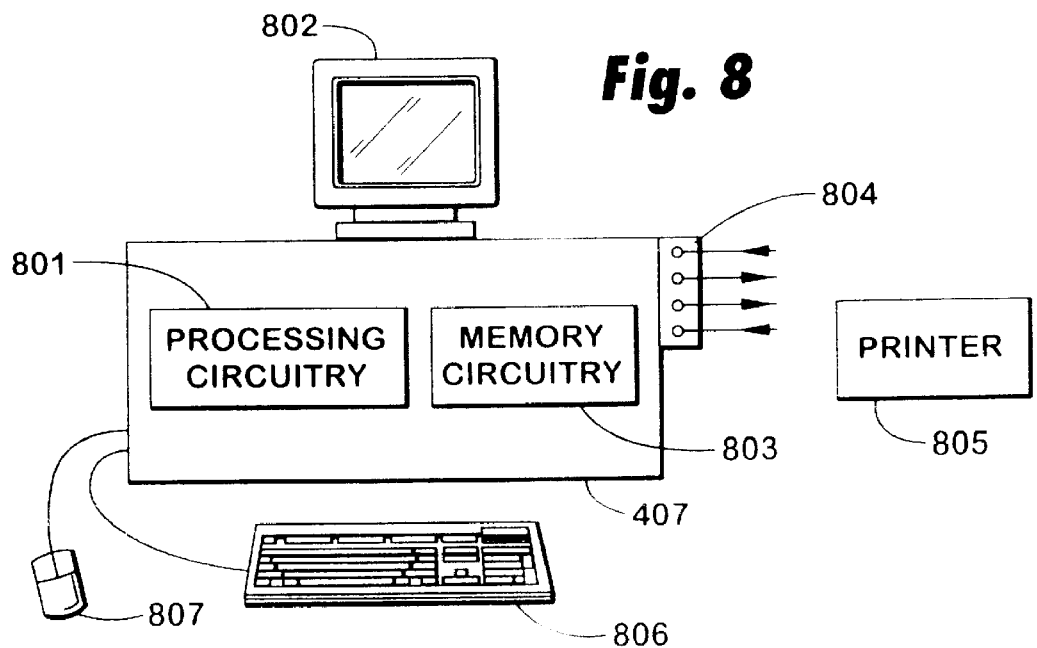
FIG. 8 is an embodiment of a processor subsystem.

Referring to FIG. 8, the main elements of processor subsystem 407 are shown. Fundamentally, processor subsystem 407 may include processing circuitry 801, memory circuitry 803 and port 804. Processing circuitry 801 and memory circuitry 803 are used for receiving, executing and implementing computer instructions. The processing circuitry 801 typically comprises a PC microprocessor system, although any combination of single or multiple microprocessors or instruction fetch and execution circuitry will suffice. The memory circuitry 803 is contemplated as a conventional PC combination of DRAM and SRAM circuits. Of course the invention may be implemented using any electronic, magnetic or other memory option. Port 804 is the gateway between processor subsystem 407 and the outside world. The processor subsystem 407 may also include interface elements such as monitor 802, keyboard 806, mouse 807 and printer 805. Any conventional computer may be adapted for use as processor subsystem 407.

4.1.3 Camera Subsystem and Camera assembly

Figure 7:
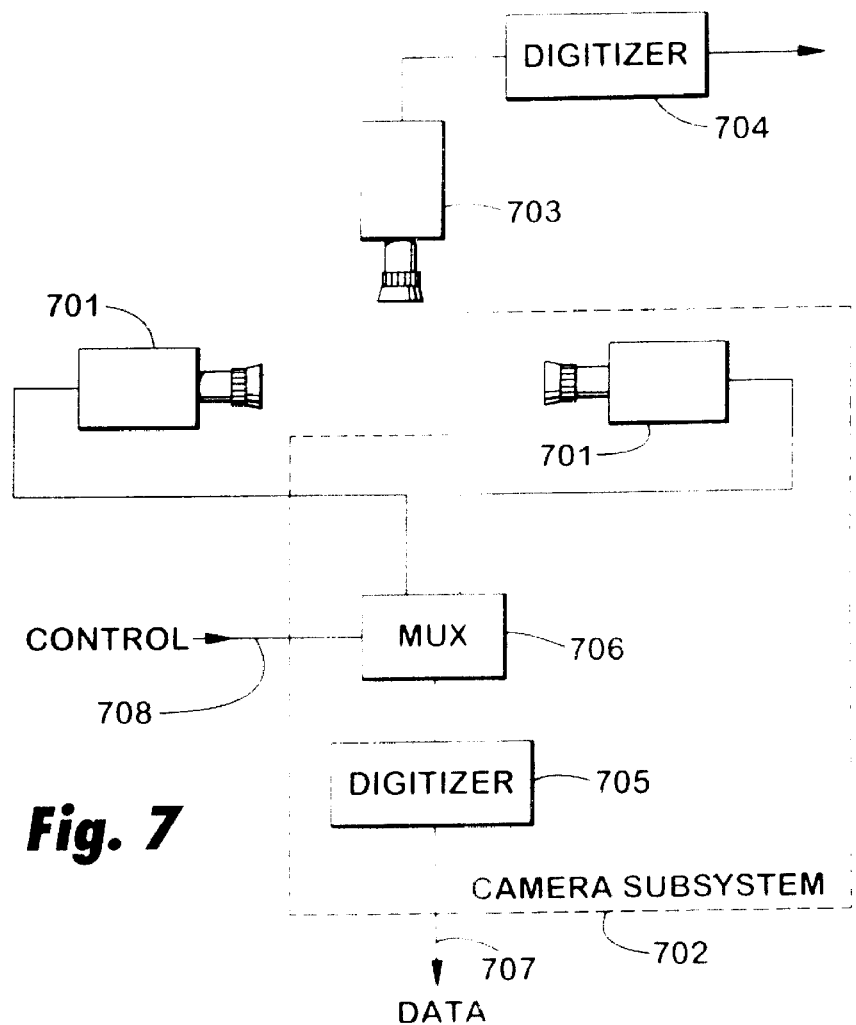
FIG. 7 is a three camera embodiment of the invention.

The invention contemplates the use of digital signal processing. Therefore, it is appropriate to represent the video images digitally. To fulfill this function, the system may employ a camera subsystem contained in an overall camera assembly. Referring to FIG. 7, a camera assembly having three camera subsystems is shown. In function, a camera subsystem 702 receives an image and then represents that image in digital form. The digitized image is then passed on to processor subsystem 407 via data line 707. A camera subsystem 702 may contain the following: (1) a camera 701 or other device suited to receive images; and 2) a digitizer 705 or other means for creating a digital representation of the received images, e.g. a CCD or analog-to-frame-grabber arrangement. A camera subsystem 702 may also contain a multiplexer. The multiplexer functions to select one of two side view cameras 701 in a three camera embodiment of the multi-camera system. The multiplexer is controlled by a processor subsystem 407 via control line 708. It is noteworthy that any part or all of a camera subsystem 702 may also be part of a processor subsystem 407.

4.1.4 Other Embodiments

One skilled in the art, will, of course, recognize that this invention is not restricted by the specific embodiment presented here. For example, a pattern may be reflected off the eye by using a placido or any other reasonable means such as L.E.D.s or fiber optics. Furthermore, the invention is not strictly limited to the examination of a human eye. The invention may also be used to obtain topography information about any eye or similarly shaped object such as a ball bearing, calibration sphere, contact lens or artificial tears. Moreover, images may be captured by means other than cameras. For example any CCD array or analog camera type device may be used.

4.2 Auto-positioning; Aligning the Apex

Figure 1:
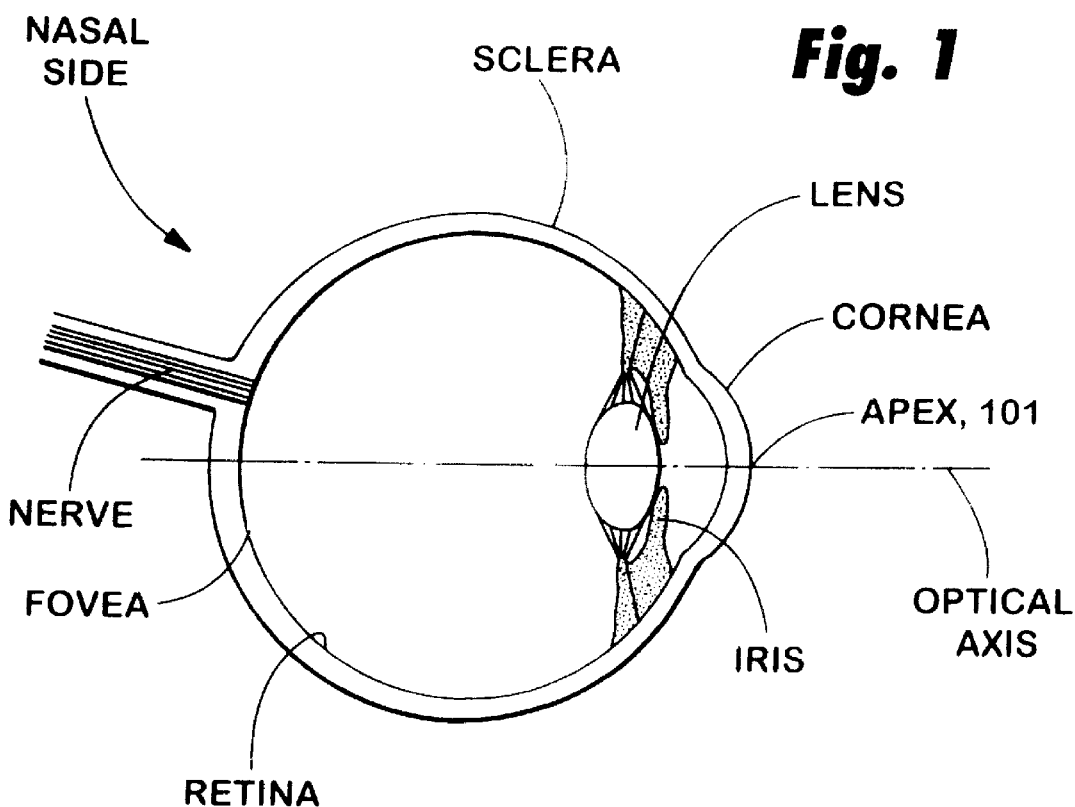
FIG. 1 is profile of a human eye.

In prior art corneal topography systems, the apex of the eye is aligned with the optical axis of the camera through various conventional techniques. Generally, none of these techniques can provide a precise alignment because, when only a front-view camera is employed, the system must estimate the Z-axis location of the apex. The current invention addresses this problem by precisely locating the apex via a side-view camera. Specifically, as previously discussed, a side-view camera according to the invention can capture an image of the true corneal profile, e.g. FIG. 1 shows a drawing of a corneal profile and FIG. 6 shows an actual photo of the same. Given the side-view corneal image, the apex is identified as the leading edge of the profile. For example, apex 101 is found at the leading edge in the corneal profile of FIG. 1.

Applying this concept to the disclosed embodiments, side-view camera 404 captures an image of the corneal profile. The image is digitized by a digitizer in the camera 404's subsystem. The apex, or leading edge, is then located according to the procedures in the supplemental disclosure to this specification. More particularly, processor subsystem 407 receives digitized images of both front and side views. Using the front view, processor subsystem 407 may determine the expected location of the apex in three dimensions (X, Y and Z) and the actual location in 2 dimensions (X and Y). As indicated above, using the side view, processor subsystem 407 may determine the actual Z-axis location of the apex. Having both the expected and actual location, processor subsystem 407 may generate an error signal indicating or representing the locational difference between the true and expected locations of the apex. Given the foregoing information, processor subsystem 407 may also generate a signal indicating or representing the position of the apex relative to an X, Y, Z coordinate system such as the system defined by point 408 and the intersection of side-view optical axis 405 with front-view optical axis 406. Of course, all the described activity may be visually represented on monitor 802 or by printing of printer 805.

4.2.1 Closed-loop positioning

Figure 9:
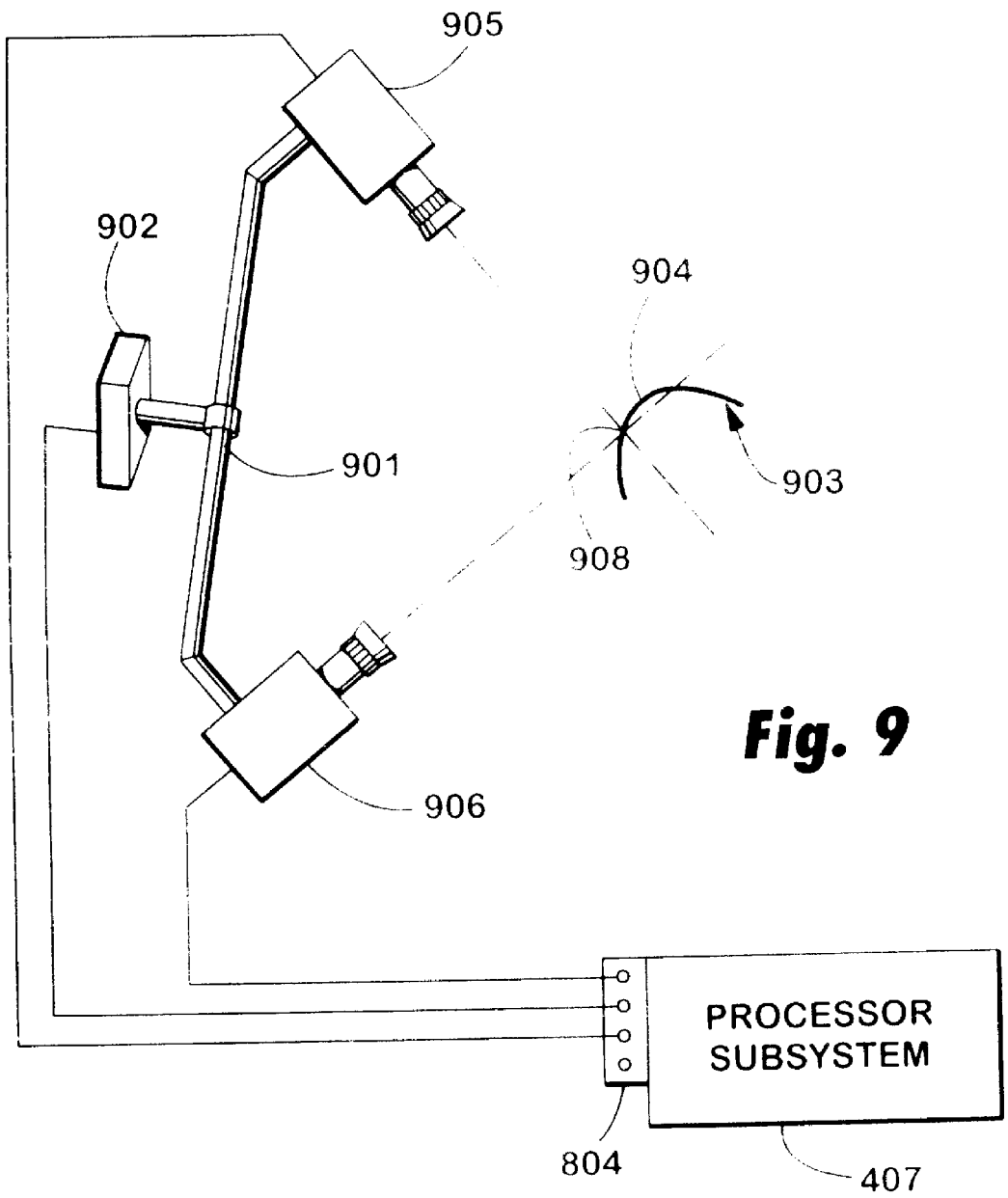
FIG. 9 is a two camera embodiment of the invention.
Figure 3:
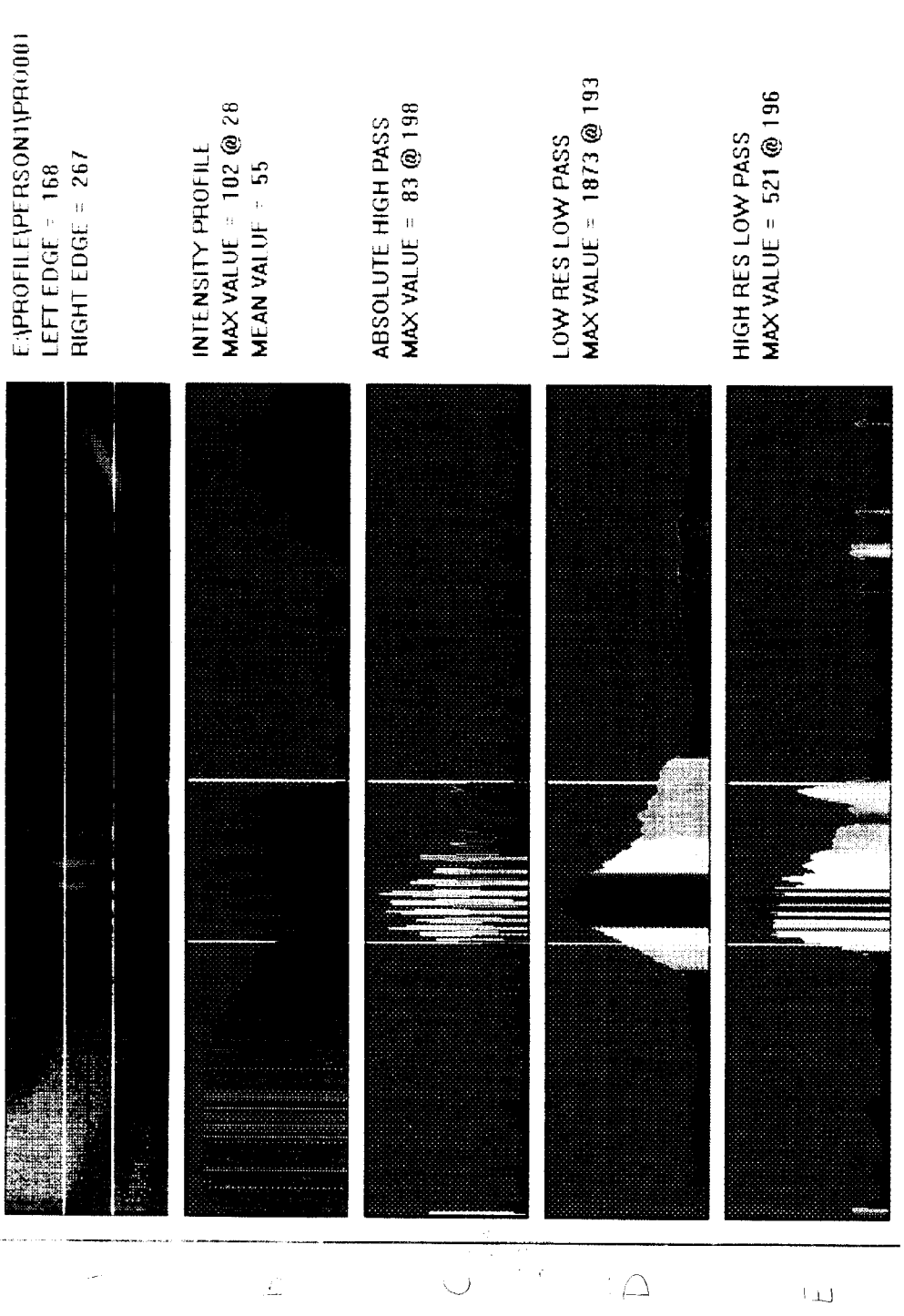
Figure 2:
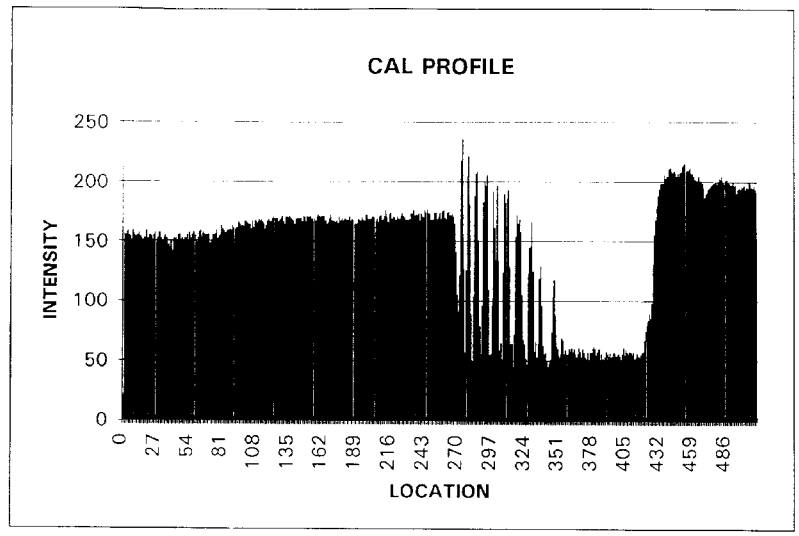
Figure 7:
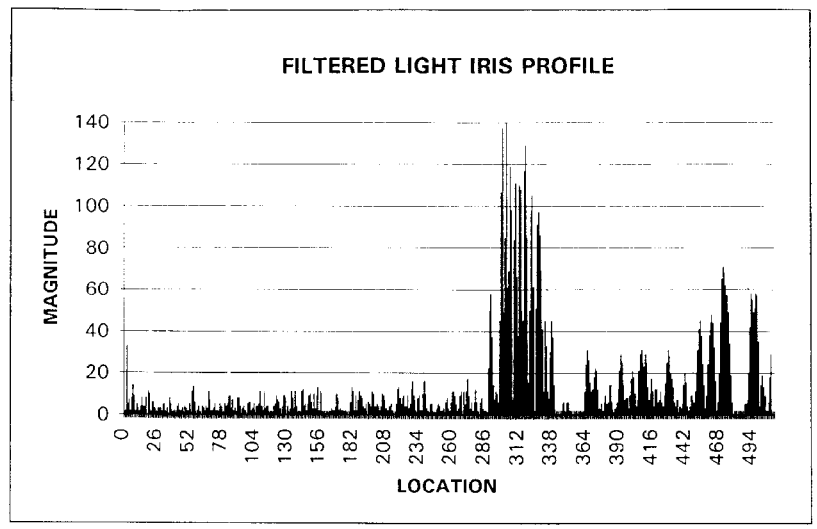
Figure 8:
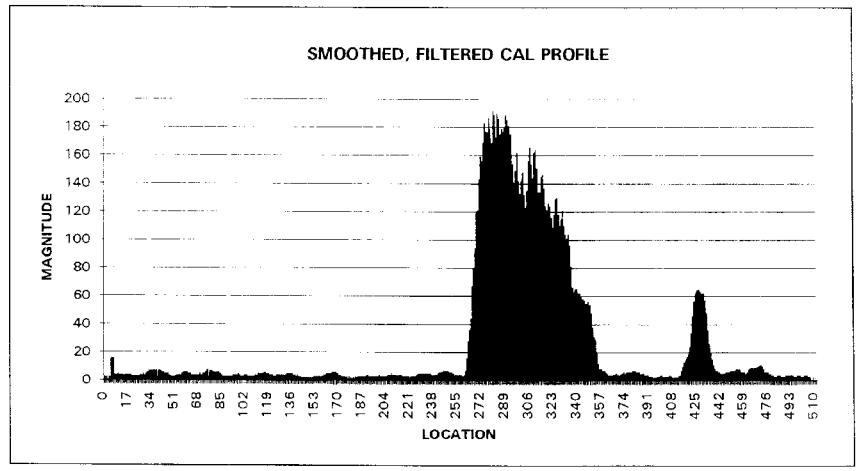
Figure 9:
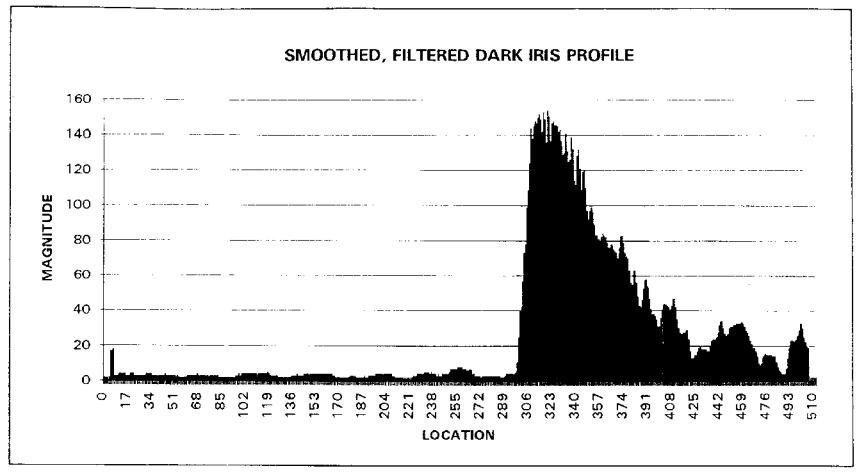
Figure 10:
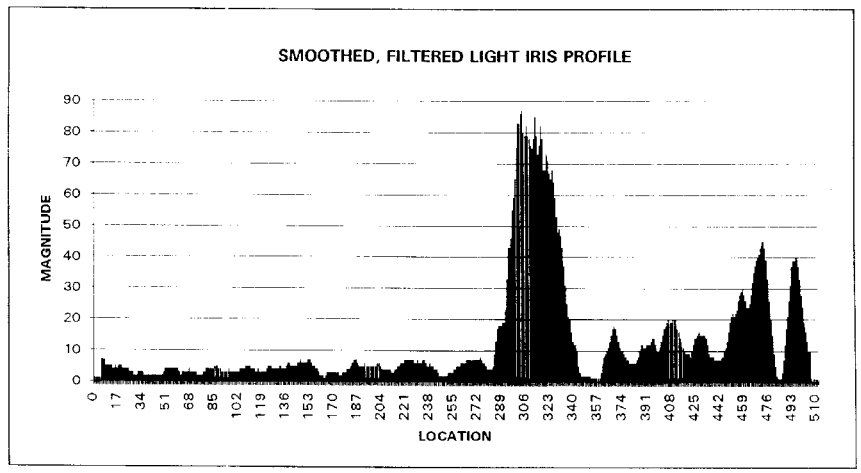
Figure 11:
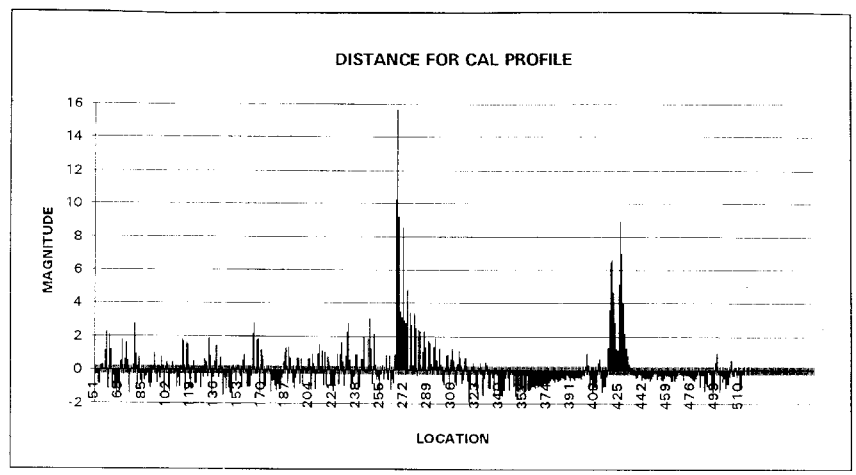
Figure 12:
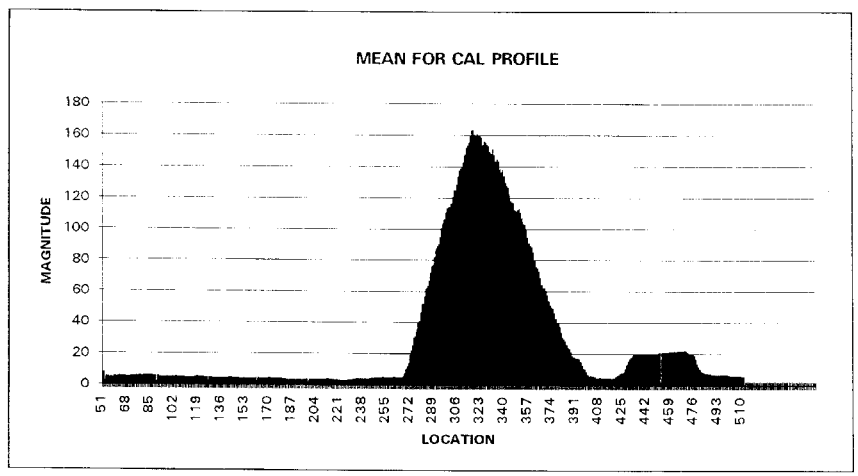
Figure 13:
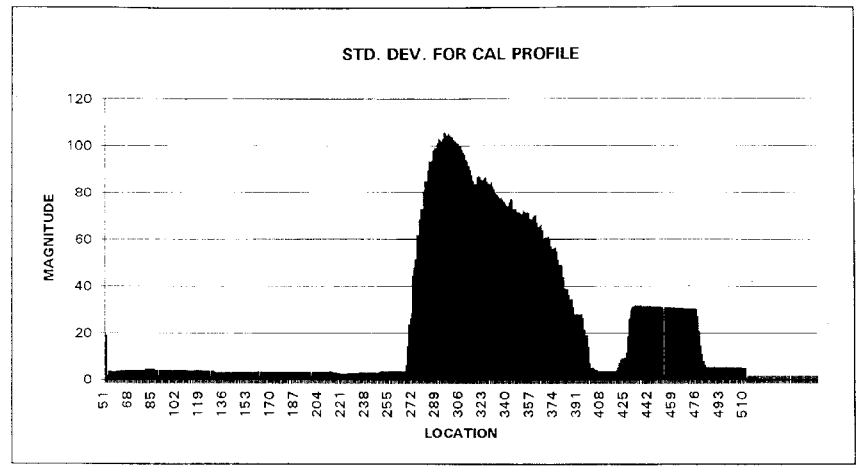
Figure 14:
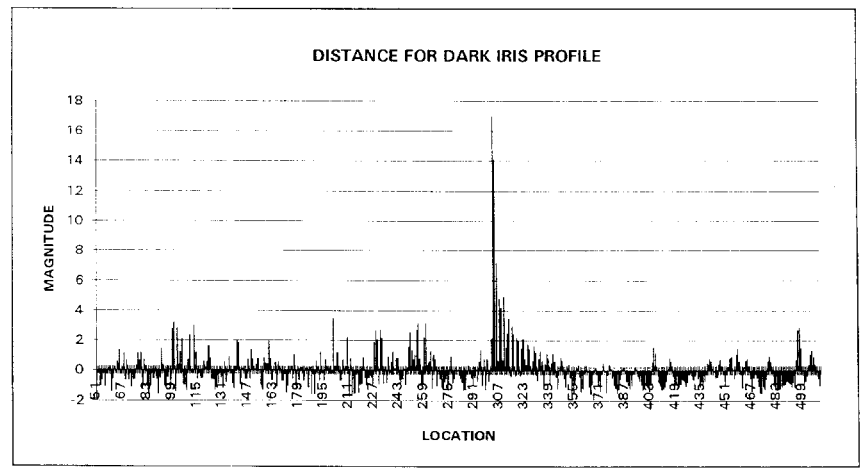
Figure 15:
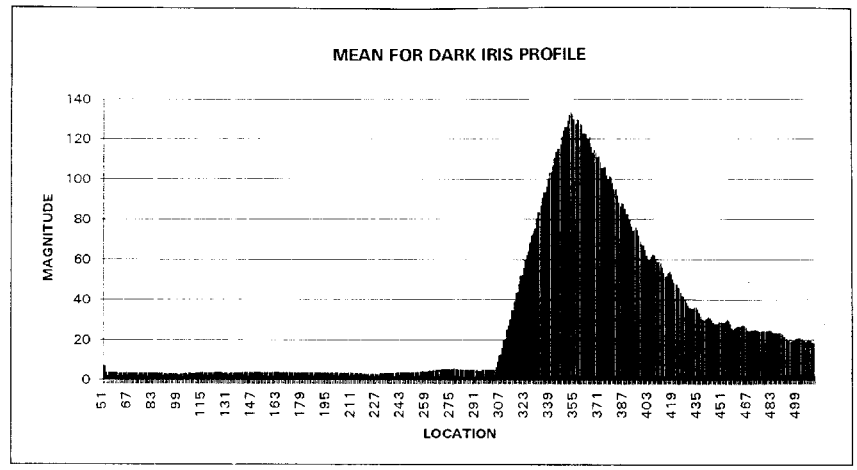
Figure 16:
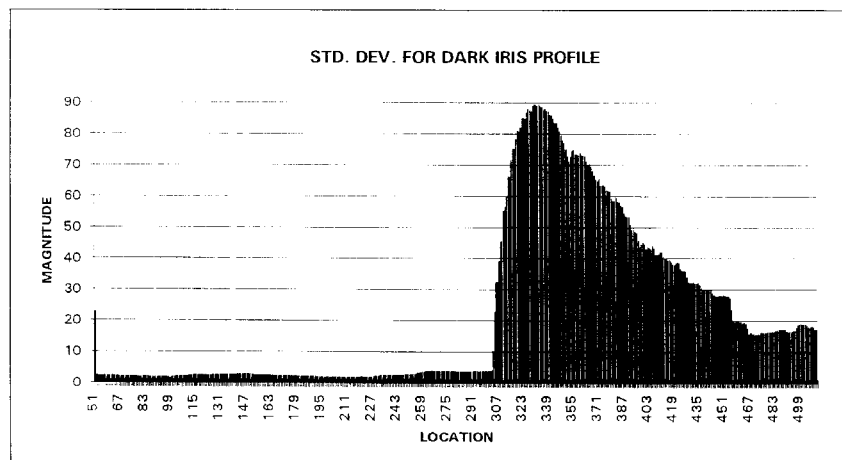
Figure 17:
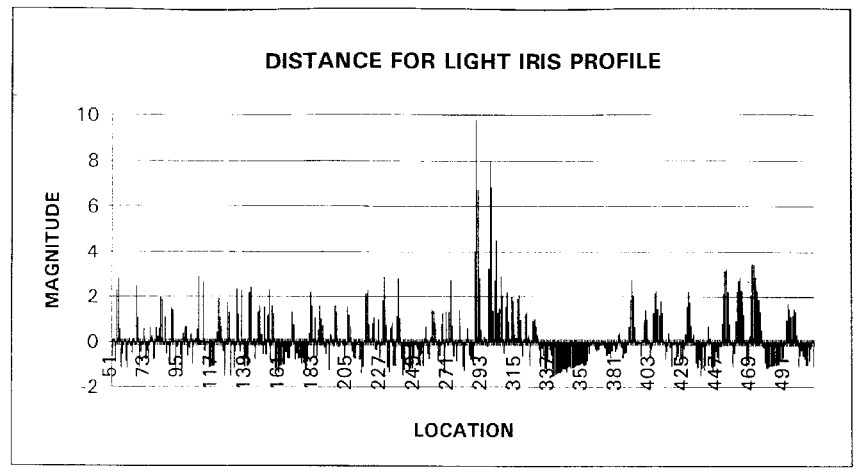
Figure 18:
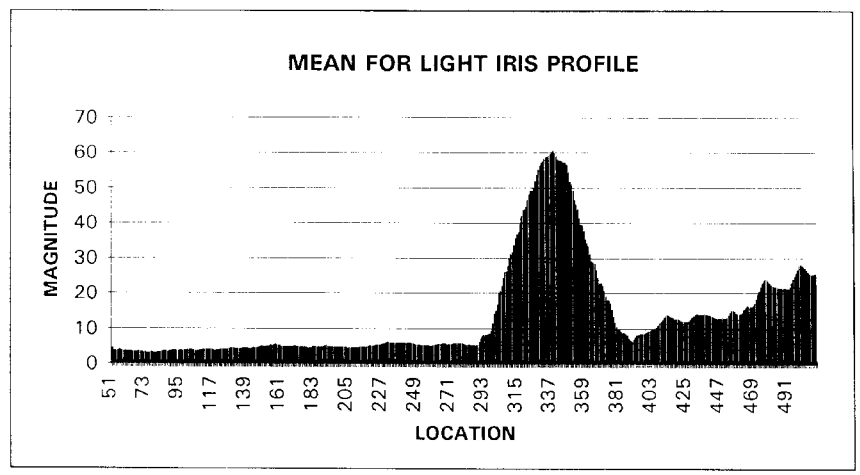
Figure 19:
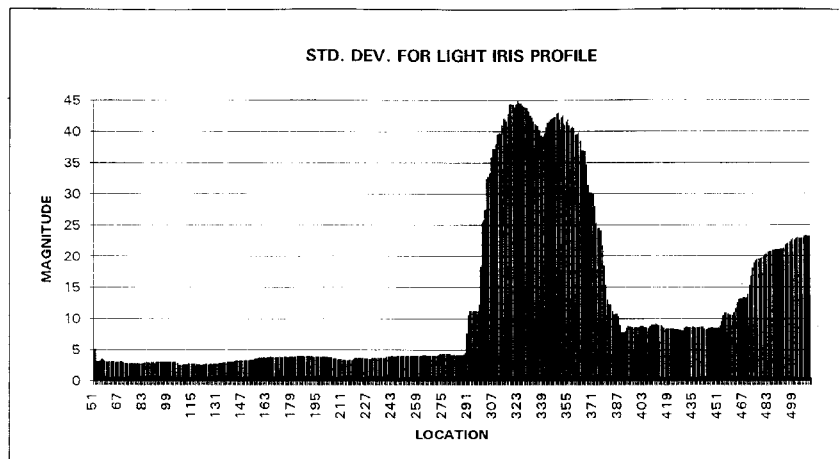
Figure 21:
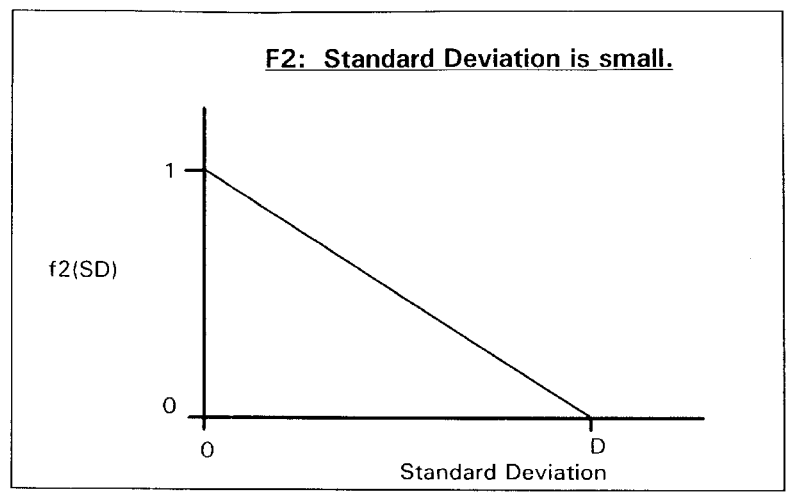
Figure 22:
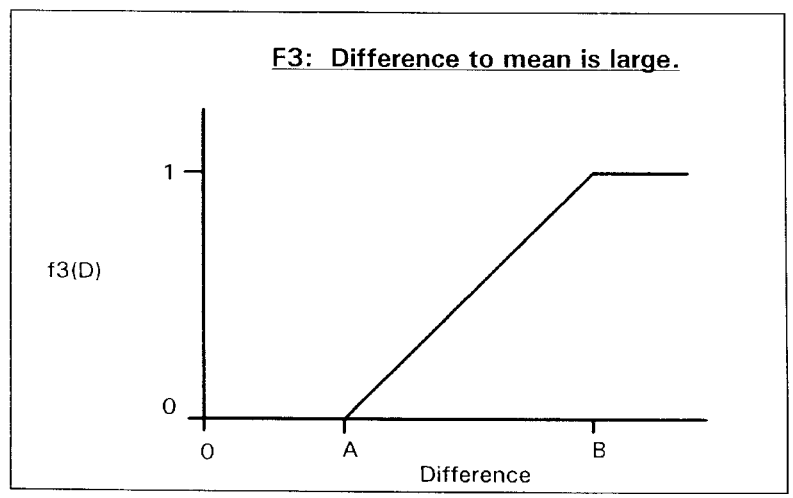
Figure 23:
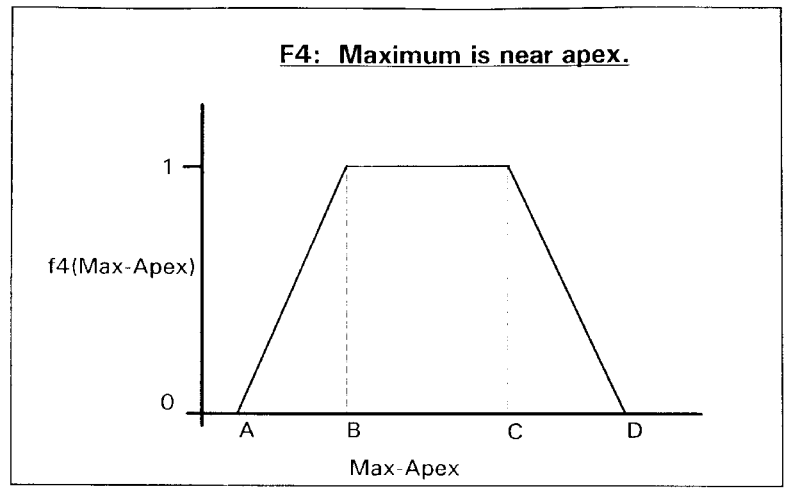
Figure 24:
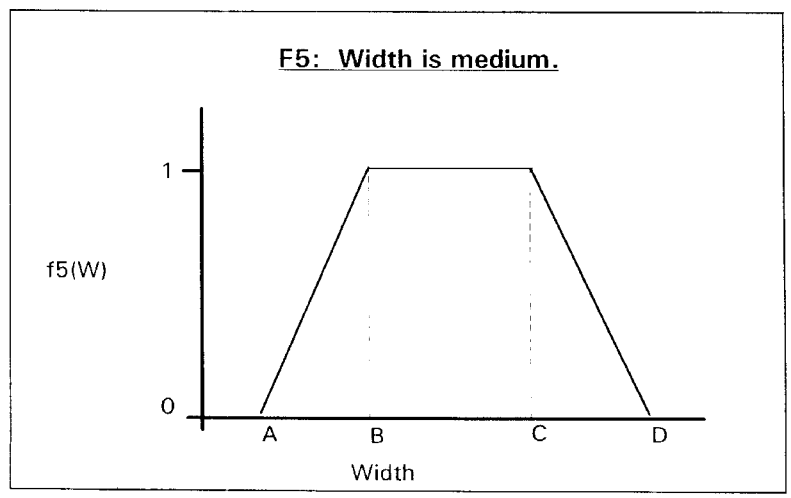
Figure 25:
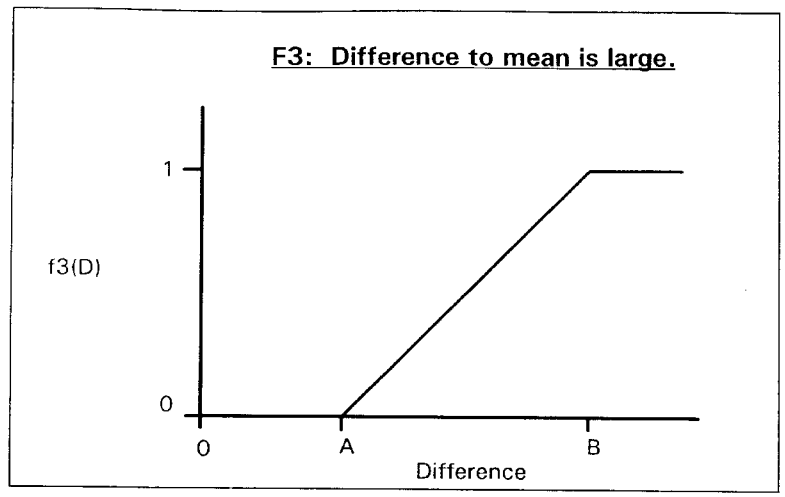
Figure 26:
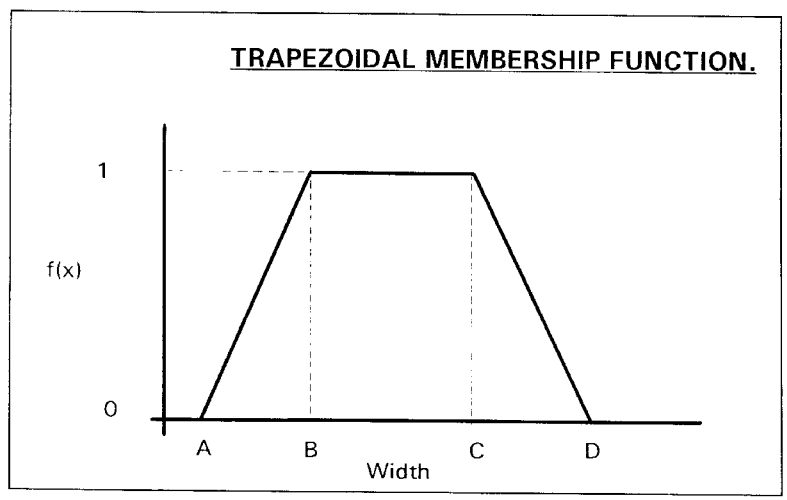

The invention contemplates using the described error signal to physically change the position of the camera assembly so that the apex of the eye (or other unit under test) is aligned with the optical axis of the front-view camera. This position may be changed either manually or automatically. Referring to FIG. 9, front-view camera 905 is connected to side-view camera 906 by rigid connection 901. Furthermore, mechanical controller 902 has a moving arm that is firmly coupled to rigid connection 901. This overall assembly allows mechanical controller 902 to move the camera assembly without changing the relative positioning between front-view camera 905 and side view camera 906.

In operation, front-view and side-view images are captured and digitized. The digitized images are processed in processor subsystem 407 and an error signal is generated representing the actual position of apex 904 relative to the desired position for the apex. The desired position is typically at origin 905 which is the intersection of the optical axis. However, the desired position may be elsewhere, e.g. the system may simply seek to align a single optical axis with the apex.

The error signal is used, either directly or indirectly, to control the actuation of mechanical controller 901. Upon receiving an actuation signal, mechanical controller 901 will alter the position of the camera assembly. For higher accuracy this process may be iterated until the apex is positioned precisely as desired. Of course, the error signal may be used in other ways. For example, the error signal may be used for the following purposes: 1) to correct calculations (such as radius of curvature) made on an eye (or other unit under test) that is not ideally positioned relative to the cameras; or 2) to generate a graphical representation of the error to display on a monitor or printer. These uses of the error signal are further discussed in the context of specific embodiments in appendixes 1 and 2.

4.3 Finding Curvature Using The Side-View Camera

As mentioned earlier, a side-view image allows calculation of radius of curvature, along the horizontal, up to the limbus. The calculation is facilitated by the side-view camera's capture of the reflected placido pattern (typically rings). Furthermore, curvature is ultimately determined by collecting data from an eye (or other unit under test) and interpolating the collected data with similar data taken from objects having known radii of curvature.

Specifically, the process begins by collecting a reference set of reflecting surfaces (calibration balls) having known radii of curvature. The reference set should include enough balls of varying size to create a scale large enough and granular enough so that accurate interpolation is possible against data taken from the intended class of units under test. Each ball may be placed under test, for example by (i) reflecting rings off the ball, (ii) capturing an image of the ball with a side view camera, and (iii) measuring the distance from the apex to the edges of all the rings (or measuring the distance between adjoining ring edges). The measured distances may be cataloged with the corresponding radius of curvature of the examined ball. Once all the balls are examined, a full table may be constructed revealing radius of curvature versus distances (either apex to various edge or edge to edge). Finally, when an eye (or other unknown unit under test) is examined, the apex to edges (or edge to edge) distances may again be measured and the radius of curvature may be calculated by linear or other interpolation with the collected data.

4.4 Locating The Limbus

The multi-camera system may also be used to find the location of the limbus in three space (X,Y,Z). The Z-axis position of the limbus is obtained with the side-view camera. Once a side view image is obtained, a point on the limbus edge can be found by locating the transition from homogeneous white region to non-homogeneous region on any horizontal line in the side view corneal image. All the relevant points along the limbus may be located in this same manner.

A real image from the front camera may then be used to locate the limbus' Y-axis and X-axis position. Once again, the limbus is located by finding the transition from homogeneous white region to non-homogeneous region. Through this process, the limbus if finally located in three space.

It is noteworthy that locating the limbus may be conveniently accomplished by digitizing the captured images. Since the limbus will always embody a transition from homogeneous white region to non-homogeneous region, the limbus is easily located through various image processing techniques. For example, an intensity profile of the image will show white regions as low energy regions and reflected ring regions as high energy regions. Therefore the location of the limbus will correspond to the transition from a high energy to a low energy region.

4.5 Finding A Profile

A corneal profile may be located by using the multi-camera system. Specifically, a profile along the horizontal meridian is found by using a virtual image (the reflected pattern) obtained through the side-view camera. The virtual image is digitized (to create an intensity profile) and then high pass filtered. The profile is then located at the near-camera boundary between a high energy region and a low energy region. This process is described in detail in appendix 1.

4.6 Additional Disclosure

As supplemental disclosure, the following has been provided: 1) Appendix 1 containing a draft paper written by an inventor (Dr. Sarver); and 2) Appendix 2 containing inventor's documentation.

DRAFT
E. SARVER

EYESYS MULTI-CAMERA CORNEAL TOPOGRAPHY

REAL-TIME APEX DETECTION ALGORITHM

ED SARVER, PH.D.
GRAPHICS AND IMAGE PROCESSING CONSULTANT
18 BOGART PLACE
MERRITT ISLAND, FL 32953
(407) 453-3533

OCTOBER 18, 1994

DRAFT
E. SARVER

HISTORY

10/18/94:    Ed Sarver

Initial release.

DRAFT
E. SARVER

CONTENTS 1.0 INTRODUCTION .................................................................................... 4
2.0 SYSTEM CHARACTERISTICS ............................................................. 4
3.0 ALGORITHM DERIVATION .................................................................. 5
    3.1 Top Level Description ..................................................................... 6
    3.2 Analysis Row Acquisition ................................................................ 8
    3.3 Edge Operator ................................................................................. 9
    3.4 Rings Locator ................................................................................ 10
    3.5 Apex Locator ................................................................................. 12
4.0 IMPLEMENTATION DETAILS ............................................................ 14
    4.1 Box Filters ..................................................................................... 14
    4.2 Computation Complexity .............................................................. 14
        4.2.1 Edge Enhancement ............................................................ 14
        4.2.2 Low Resolution Moving Sum ............................................. 15
        4.2.3 High Resolution Moving Sum ............................................ 15
        4.2.4 Complexity Summary ......................................................... 16
    4.3 Real-time Performance ................................................................. 16
5.0 EMPIRICAL EVALUATION ................................................................. 16
    5.1 Subjects ......................................................................................... 16
    5.2 Evaluation Method ........................................................................ 17
    5.3 Results ........................................................................................... 17
6.0 SUMMARY AND RECOMMENDATIONS ........................................... 17
    6.1 Summary of Algorithm Goals and Results .................................. 18
    6.2 Recommendations for Final Test and Quality Control ............... 18
    6.3 Recommendations for Marketing Claims .................................... 18
    6.4 Recommendations for Further Tests and Improvements .......... 18
        6.4.1 Computation Reduction ..................................................... 18
        6.4.2 Measurements to Limbus .................................................. 18
        6.4.3 Profile of Vertical Meridian ................................................ 19
        6.4.4 Improving Reliability of Algorithm ................................... 19
    6.5 Recommended Research and Publications ................................ 19
        6.5.1 Accuracy Studies ............................................................... 19
        6.5.2 Cornea Shape Study .......................................................... 19
        6.5.3 IR Illumination Study ......................................................... 19
7.0 REFERENCES ..................................................................................... 20
APPENDIX A: C++ FUNCTION LISTING .................................................. 21
APPENDIX B: DATA SHEET FOR ALGORITHM EVALUATION ............. 22
APPENDIX C: EYELASH MEASUREMENTS ........................................... 23
APPENDIX D: RESULTS FOR ALL SUBJECTS ....................................... 24

DRAFT
E. SARVER

EYESYS MULTI-CAMERA CORNEAL TOPOGRAPHY

REAL-TIME APEX DETECTION ALGORITHM

ED SARVER, PH.D.

1.0 INTRODUCTION

Corneal topography provides a method for measuring the refractive power of the cornea over most of its optically active part [3]. The goal of this algorithm is to provide accurate and reliable detection of the corneal apex as recorded in the temporal view image array of the EyeSys multi-camera corneal topography system. We will consider computation complexity, real-time performance in the Peripheral Corneal Topography System (PECTS) environment, and the empirically determined accuracy and reliability of the algorithm.

The basic idea for the multi-resolution detection/estimation algorithm is to operate on a profile of pixels extracted from the temporal view array such that (1) the edges are enhanced, (2) the region of rings reflected off the cornea is detected, and (3) the edge of the reflected rings region is estimated. Details of this process is provided in the following.

2.0 SYSTEM CHARACTERISTICS

General characteristics of the temporal image are listed below:

- Digitized from a monochrome NTSC signal at 8 bits per pixel.
- Array size is 480 rows by 512 columns.
- Horizontal resolution is 20 microns / pixel (For a general discussion of digital images, see [5].)

The temporal view of the OS cornea is illustrated in Figure 1.

DRAFT
E. SARVER

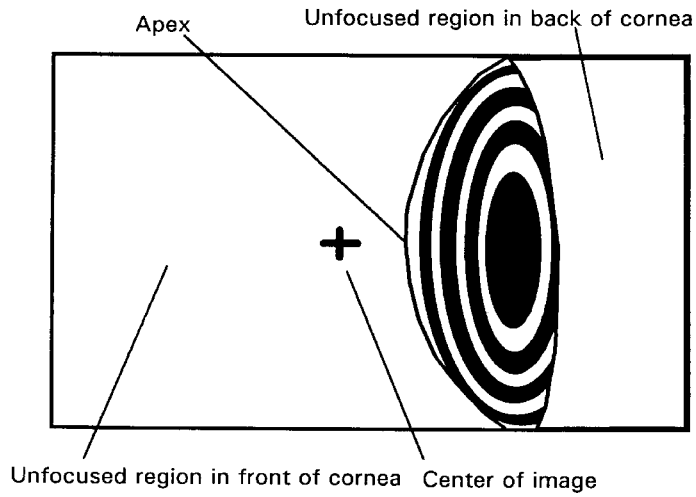

FIGURE 1.

We will refer to the unfocused region in front of the cornea as region A; the focused region of reflected rings on the cornea as region B; and the unfocused region in back of the cornea as region C. Our goal will be to determine the location of the apex with respect to the center of the image. We will refer to a "profile" as the sequence of intensity values for a given row of the image.

3.0   ALGORITHM DERIVATION

In this section we will derive the algorithm by considering sequential operations starting from the temporal image and concluding with a column number indicating the location of the apex of the cornea at row 240 of the temporal image array. We begin with a top level description of the algorithm.

Variables used in the following sections are:

NUM_COLS_SIDEVIEW:  Number of columns in the temporal image: 512

D_WIDTH:  Half-width of difference filter: 2

LR_WIDTH:  Width of low resolution integration filter: 20

HR_WIDTH:  Width of high resolution integration filter: 4

DRAFT
E. SARVER m0: Row to use in location of apex: 240 y[n]: Starting one-dimensional array for use in detection analysis. It consists of the average of M1 rows spaced W1 rows apart.

d[n]: Edge enhanced array.

u[n]: Low resolution local edge energy array (integrator).

v[n]: High resolution local edge energy array (integrator).

valueDiff: Edge array maximum (for display only)

valueLR: Low resolution integrator maximum value.

indexLR: Location of low resolution integrator maximum valueHR: High resolution integrator maximum value indexHR: Location of high resolution integrator maximum value edgeRightLR: Right edge of low resolution peak region.

edgeLeftLR: Left edge of low resolution peak region.

edgeRightHR: Right edge of high resolution region.

edgeLeftHR: Left edge of high resolution region.

3.1 Top Level Description

Figure 2:
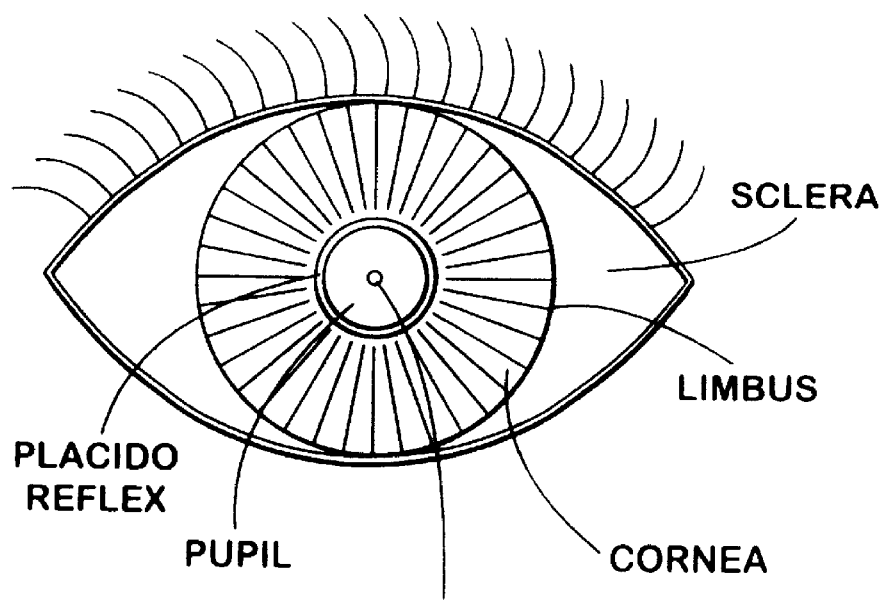
FIG. 2 is a front-view of a human eye.

In this section we will present a top level description of the algorithm and provide details in the following. The basic idea of the algorithm is illustrated in Figure 2. The steps are:

1. Compute the one-dimensional analysis array, y[n], using three rows from the temporal image array.

2. Enhance the edges in the y[n] vector and store the results in vector d[n].

3. Compute a sliding sum of the edge vector d[n] and store the results in u[n]. Compute a higher resolution version of u[n] by using a smaller

DRAFT
E. SARVER neighborhood to compute a sliding sum of d[n] and store the results in v[n].

4. Find the maximum value and its location from u[n]. Call this maximum valueLR and the location of the maximum is indexLR. Starting at the maximum, find the left and right points (denoted edgeLeftLR and edgeRightLR) where the value of u[n] drops to valueLR/3.

5. Find the maximum value of v[n]. Call this maximum valueHR and its location indexHR. Next, starting at the index corresponding to edgeLeftLR, find the first point in v[n] to the right of edgeLeftLR where v[n] is greater than valueHR / 3. Call the index of this point edgeLeftHR. Then, starting at the index corresponding to edgeRightLR, find the first point to the left of edgeRightLR where v[n] is greater than valueHR/3. Call the index of this point edgeRightHR.

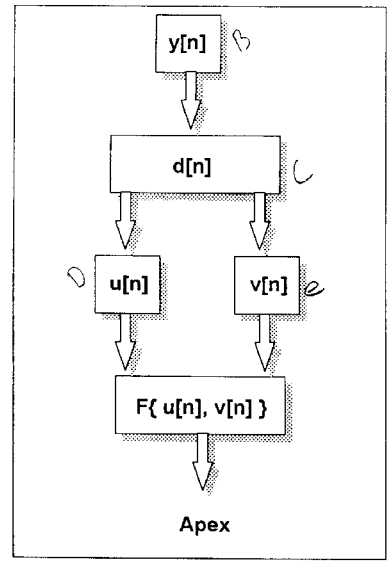

FIGURE 2.

The final values of these five steps, edgeLeftHR and edgeRightHR, identify the estimated bounds for the reflected rings region (region B in Figure 1). By knowing which eye we are processing, OS (left) or OD (right), we will know which one is the apex location according to:

DRAFT
E. SARVER

- If we are processing OD, the apex is identified by edgeRightHR
- If we are processing OS, the apex is identified by edgeLeftHR

A detailed description of these steps are provided in the following sections and a C++ class listing for the algorithm (assuming y[n] is already computed) in provided in Appendix A. (A good reference on C++ is [1].)

In the C++ listing and in the code fragments which follow, the variable names used are the same as those described above with the following exceptions:

y[n] = imageBuff[n]
    d[n] = diffBuffer[n]
    u[n] = sumLRBuffer[n]
    v[n] = sumLRBuffer[n]

3.2 Analysis Row Acquisition

Since minimizing computation is a major design goal of this algorithm, we will perform most of our analysis on a one-dimensional vector, denoted y[n]. The array y[n] is the average of the three temporal image intensity rows at j=m0-M, m0, and m0+M. Thus, $$y[n] = \frac{x[240-M,n] + x[240,n] + x[240+M,n]}{3}$$

where M = 15, and m0 = 240. To determine the value of M, we measured eyelashes present in several images (see Appendix C). Using this technique, it was found that the average width of an eyelash is 13.1 pixels. We slightly increase the value of M to account for larger than average lashes and set its value to 15. It should be noted that more than one eyelash can be present in the analysis area on the cornea. If several eyelashes are clumped together, e.g. as in a blink, the reflected rings will not be visible on the cornea. In fact, the cornea and its apex may be almost entirely occluded. It this case it will not be possible to detect the corneal apex using the algorithm described here (see section 6 for a discussion of possible solutions to this situation).

An example of this step is given in Figure 3. In this figure, (a) shows the rows around the center row. The green line locates the center row, and the two yellow lines show the location of the other rows used to generate the y[n] array. The y[n] array is shown in (b). The intensity of the vertical

DRAFT
E. SARVER line in (b) is the same as the value y[n] and the height used to plot the line is directly proportional to y[n].

The C++ class listing in Appendix A assumes this calculation is already accomplished prior to calling the member function GetApex().

3.3 Edge Operator

The purpose of the edge operator is to determine where the rings reflect off the cornea. These ring edges exhibit sharp contrast and hence can be enhanced using a simple edge operator as indicated in the following:

$$d[n] = \left| \sum_{k=-W_1}^{W_1} y[n-k]h[k] \right|$$

$$h[k] = \{-1, \ldots -1, 0, 1, \ldots 1\}$$

or $$d[n] = \left| \sum_{k=1}^{W_1} y[n+k] - \sum_{k=1}^{W_1} y[n-k] \right|$$

where W1 is set to D_WIDTH. The size of W1 (2) is set to a size that reduces noise effects while at the same time is small enough to fit in between small ring reflections. The absolute value operator is used to simplify the computation to follow. Note that h[n] is a zero-phase high pass filter [4].

The C++ code fragment for this function is:

```
//        -------- get edge enhancement --------
         m_ap->valueDiff = -1.;
         m_ap->indexDiff = 1;
         for (i=D_WIDTH; i<NUM_COLS_SIDEVIEW-D_WIDTH; i++) {
                  sum1 = 0.;
                  sum2 = 0.;
                  for (j=1; j<=D_WIDTH; j++) {
                           sum1 += (double) imageBuff[i+j];
                           sum2 += (double) imageBuff[i-j];
                  }
                  t = sum1 - sum2;
                  if (t<0.) t = -t;
                  m_ap->diffBuffer[i] = t;
                  if (t>m_ap->valueDiff) {
                           m_ap->valueDiff = t;
                           m_ap->indexDiff = i;
```

DRAFT
E. SARVER

>
>        >

The minimum index for imageBuff is (D_WIDTH - D_WIDTH) = 0.

The maximum index for imageBuff is (NUM_COLS_SIDEVIEW-D_WIDTH+D_WIDTH) - 1 = NUM_COLS_SIDEVIEW - 1

Thus, the array is not addressed out of bounds.

Figure 3(c) shows a plot of d[n]. The plot is normalized such that the maximum value used is 90% of the available plot window height. The height of each line is proportional to the value of d[n]. The color of the lines are selected such that (1) for d[n] = 0, the line is blue; (2) for d[n] = valueDiff/2, the line is green, and (3) for d[n] = valueDiff, the line is red. For values in-between these, the color is selected such that the hue angle is linearly interpolated, the saturation is set to 1, and the value is maximum, i.e. 255 (see [2] for a discussion of the HSV color space).

3.4 Rings Locator

Since the largest concentration of edge energy is expected to be in the neighborhood of the cornea, we apply a large moving sum of the edge operator array to find the location of maximum concentration of edge energy. The moving sum is computed according to:

$$u[n] = \sum_{k=-W_2}^{W_2} d[n-k]$$

where W2 is set to LR_WIDTH (20). The size of W2 was empirically determined by considering the size of the neighborhood of reflected rings on the cornea as seen in the temporal images. The maximum value for u[n] is found and is used as an indication of the rough location of the cornea. This maximum is denoted valueLR.

Starting at the location of the maximum, indexLR, we search left and right to find the edges of the region of rings reflected on the cornea. The search is carried out until the value of u[n] falls below valueLR/3. For an ideal situation, i.e. one where d[n] only has non-zero values at ring edges on the cornea and these values are all equal, the edges will be where the value is valueLR/2. Thus, the search proposed will go a little past the

DRAFT
E. SARVER edge. We will then fine tune the edge location using the operation indicated in the next section.

The C++ code fragment for the low resolution moving sum is:

```
//          -------- get low resolution moving average -------- sum = 0.;
     for (i=0; i<2*LR_WIDTH+1; i++)
             sum += m_ap->diffBuffer[i];

m_ap->valueLR = -1.;
     m_ap->indexLR = 1;
     for (i=LR_WIDTH; i<NUM_COLS_SIDEVIEW-(LR_WIDTH+1); i++) { m_ap->sumLRBuffer[i] = sum;
             if (sum > m_ap->valueLR) {
                     m_ap->valueLR = sum;
                     m_ap->indexLR = i;
             } sum += m_ap->diffBuffer[i+LR_WIDTH+1];
             sum -= m_ap->diffBuffer[i-LR_WIDTH];
     }
```

In the computation of the moving sum, we use the variable sum. The concept here is like a one-dimensional box filter (see section 4.1). Prior to the next loop, we add in the next value not used in the sum and subtract off the last value. This reduces the number of adds for each loop from 41 to 2. The bounds on the index for sumLRBuffer[n] is the same (or less) as for diffBuffer[n] in the previous section, so we are OK here. The minimum value of the index for diffBuffer[n] in this loop is:

$$LR\_WIDTH - LR\_WIDTH = 0$$

The maximum value (at the sum += statement) is $$(NUM\_COLS\_SIDEVIEW-(LR\_WIDTH+1)+LR\_WIDTH+1) - 1 = NUM\_COLS\_SIDEVIEW - 1$$

This accounts for the extra +1 in the loop terminal count.

The C++ code fragment for the edge finding is self documenting. It is listed here:

```
//          -------- get left and right edge of low res array -------- t = m_ap->valueLR / 3.;
```

31

DRAFT
E. SARVER

```
m_ap->edgeLeftLR = m_ap->indexLR;
while (m_ap->edgeLeftLR>LR_WIDTH &&
       m_ap->sumLRBuffer[m_ap->edgeLeftLR]>t ) { m_ap->edgeLeftLR--;

} m_ap->edgeRightLR = m_ap->indexLR;
while (m_ap->edgeRightLR<NUM_COLS_SIDEVIEW-LR_WIDTH
&& m_ap->sumLRBuffer[m_ap->edgeRightLR]>t ) { m_ap->edgeRightLR++;

}
```

Figure 3(d) shows a plot of u[n]. The plot is normalized such that the maximum value used is 90% of the available plot window height. The height of each line is proportional to the value of u[n]. The color of the lines are selected such that (1) for u[n] = 0, the line is blue; (2) for u[n] = valueLR/2, the line is green, and (3) for u[n] = valueLR, the line is red. For values in-between these, the color is selected such that the hue angle is linearly interpolated, the saturation is set to 1, and the value is maximum (255). The maximum value, valueLR, and its location, indexLR, are shown to the right.

3.5 Apex Locator

As in the preceding operation, we apply a moving sum of the edge operator array to find the location of concentration of edge energy. The moving sum is computed according to:

$$v[n] = \sum_{k=-W_3}^{W_3} d[n-k]$$

where W3 is set to HR_WIDTH (4). The size of W3 was empirically determined by considering the size of the spacing between ring edges in the neighborhood of reflected rings on the cornea as seen in the temporal images. The maximum value for v[n], valueHR, is found and is used in the following analysis to determine the apex location.

Two searches are made on the v[n] array. First, we start at edgeLeftLR and search to the right for the first value greater than valueHR/3. This location is denoted edgeLeftHR. Next, we start at edgeRightLR and search to the left for the first value greater than valueHR/3. This location

DRAFT
E. SARVER is denoted edgeRightHR. The following rule is applied to determine which of the two is the corneal apex:

- If the temporal image is for OS (left eye), then the apex is at edgeLeftHR.
- If the temporal image is for OD (right eye), then the apex is at edgeRightHR.

The C++ code fragment for the high resolution moving sum is:

```
// --------- get high resolution moving average --------- sum = 0.;
for (i=0; i<2*HR_WIDTH+1; i++)
    sum += m_ap->diffBuffer[i];

m_ap->valueHR = -1.;
m_ap->indexHR = 1;
for (i=HR_WIDTH; i<NUM_COLS_SIDEVIEW-(HR_WIDTH+1); i++) { m_ap->sumHRBuffer[i] = sum;
    if (sum > m_ap->valueHR) {
            m_ap->valueHR = sum;
            m_ap->indexHR = i;
    } sum += m_ap->diffBuffer[i+HR_WIDTH+1];
    sum -= m_ap->diffBuffer[i-HR_WIDTH];
}
```

As with the discussion of the low resolution moving sum, the arrays stay in bounds and we employ a sum variable which is iteratively updated to reduce computation.

The C++ code fragment for the high resolution edge finding is also self documenting. It is listed here:

```
// --------- get left and right edge from high resolution array --------- t = m_ap->valueHR / 3.;

m_ap->edgeLeftHR = m_ap->edgeLeftLR;
while (   m_ap->edgeLeftHR<m_ap->indexLR &&
          m_ap->sumHRBuffer[m_ap->edgeLeftHR]<t ) { m_ap->edgeLeftHR++;

} m_ap->edgeRightHR = m_ap->edgeRightLR;
```

DRAFT
E. SARVER

```
while (    m_ap->edgeRightHR>m_ap->indexLR &&
           m_ap->sumHRBuffer[m_ap->edgeRightHR]<t ) { m_ap->edgeRightHR--;

}
```

Figure 3(e) shows a plot of v[n]. The plot is normalized such that the maximum value used is 90% of the available plot window height. The height of each line is proportional to the value of v[n]. The color of the lines are selected such that (1) for v[n] = 0, the line is blue; (2) for v[n] = valueHR/2, the line is green, and (3) for v[n] = valueHR, the line is red. For values in-between these, the color is selected such that the hue angle is linearly interpolated, the saturation is set to 1, and the value is maximum (255). The maximum value and its location is shown to the right of (e). The final locations of edgeLeftHR and edgeRightHR are indicate by the two vertical green lines. Their indices are provided to the right of (a).

4.0   IMPLEMENTATION DETAILS

In this section we will consider more details of the algorithm.

4.1   Box Filters

The "box filter" is a two-dimensional filter with equal coefficients. Ignoring initialization, an arbitrary sized filter can be computed with four operations: two to subtract off old data and two to add in new data. In our case, we only need to consider the one-dimensional version for the moving averages. We will not apply the technique to the edge enhancement filter since the extra programming steps actually increase the number of operations required for the differentiator's computation.

4.2   Computation Complexity

In this section we will count the number of operations required to compute the location of the corneal apex. This data can be used as a benchmark in future modifications which consider increased efficiency. As is typically done in this analysis, we will ignore loop control operations.

4.2.1  Edge Enhancement

The operations required for the edge enhancement are:

DRAFT
E. SARVER

- add / subtract
- absolute value
- compare

For each point we perform:

- 4 adds, 1 subtract, 1 absolute value, and 1 compare

We perform these operations on:

- N - 2*W1 = 512 - 2*2 = 508 points

This leads to:

- 2540 add / subtract, 508 absolute value, and 508 compare

4.2.2 Low Resolution Moving Sum

The operations required for the low resolution moving sum with maximum location are:

- add / subtract
- compare

For each point we perform

- 1 add, 1 subtract, 1 compare

We perform these operations on:

- N - 2*W2 = 512 - 2*20 = 472 points
- 2*W2+1 adds are used during initialization
- In addition, we perform about 2*50 compares to find the left and right edges.

This leads to:

- 985 add / subtract and 572 compare

4.2.3 High Resolution Moving Sum

The operations required for the high resolution moving sum with maximum location are:

- add / subtract

- compare

For each point we perform

- 1 add, 1 subtract, 1 compare

We perform these operations on:

- N - 2*W3 = 512 - 2*4 = 504 points
- 2*W3+1 adds are used during initialization
- In addition, we perform about 2*25 compares to find the left and right edges.

This leads to:

- 1017 add / subtract and 554 compare

4.2.4 Complexity Summary

Adding these major components together we arrive at the total of 6,684 operations as indicated in the following table:

| COMPUTATIONAL COMPLEXITY OF THE APEX DETECTION ALGORITHM | | | | |
|---|---|---|---|---|
| ALGORITHM STEP | ADD / SUB | ABS | COMPARE | OPERATIONS |
| Edge Enhancement | 2540 | 508 | 508 | 3556 |
| Low Resolution Moving Sum | 985 | 0 | 572 | 1557 |
| High Resolution Moving Sum | 1017 | 0 | 554 | 1571 |
| TOTALS | 4542 | 508 | 1634 | 6684 |

4.3 Real-time Performance

It has been empirically determined that the algorithm executes fast enough to be considered real-time (on a 90 MHz Pentium PC). This process evaluation includes the acquisition time for the image rows as well as the graphical display of the result.

5.0 EMPIRICAL EVALUATION

5.1 Subjects

To evaluate the accuracy and repeatability of the algorithm in a real-world application, we acquired 120 temporal shots for processing. These were for 20 randomly selected EyeSys employees. For each employee, three OS (left) and three OD (right) shots were obtained and stored.

DRAFT
E. SARVER

5.2 Evaluation Method

Each shot was processed using the program "sideshot". This program displays the results of each major step in the algorithm. It also allows the user to use the mouse to indicate where the algorithm missed the true apex. The distance from the computed apex to the "true" apex is displayed on the screen along with the coordinates of the mouse cursor. (This coordinate display feature allows measurement of certain features in the image. For example, this allowed the measurement of the width of eyelashes.)

The results for each shot were entered into an Excel spreadsheet where they were evaluated. This spreadsheet is listed in Appendix B.

5.3 Results

The results indicated in the spreadsheet in Appendix B are quite good. They indicate that for 120 shots the apex was measured with the following error:

| | |
|---|---|
| MIN ERROR: | -19 |
| MAX ERROR: | 4 |
| MEAN ERROR: | -0.5 |
| STD. DEV: | 2.3 | where units are in pixels. For a Gaussian assumption, this means we would expect less than 5 pixels error 95.4% of the time. For one pixel equal to 20 microns, this is less than 100 microns error 95.4% of the time.

Examination of the data and the image that led to the largest error (-19) indicates that it was a "bad" shot. If we remove this one (of 120) from consideration, the error distribution is:

| | |
|---|---|
| MIN ERROR: | -9 |
| MAX ERROR: | 4 |
| MEAN ERROR: | -0.3 |
| STD. DEV: | 1.7 |

For a Gaussian assumption, this means we would expect less than 3.4 pixels error 95.4% of the time. For one pixel equal to 20 microns, this is less than 68 microns error 95.4% of the time.

6.0 SUMMARY AND RECOMMENDATIONS

DRAFT
E. SARVER

6.1 Summary of Algorithm Goals and Results

The goal of this algorithm was to detect the corneal apex in the temporal view of a corneal topography system. This algorithm was required to be accurate and reliable as well as efficient since it was to be applied in a real-time system. The results were obtained and verified using a sample of 120 temporal shots.

6.2 Recommendations for Final Test and Quality Control

- During final system test, take a shot of an eye and process the results using "sideshot". Enter the results into the Excel spreadsheet and generate running mean and running standard deviation plots. The combination of mean +/- 2 SD should be less than 5 pixels or corrective action should be taken.

6.3 Recommendations for Marketing Claims

While the temporal views obtained contain a lot of information about the cornea (and possibly other features of the eye), the current algorithm is used specifically to determine the location of the corneal apex. Based on the initial sample of 120 shots and the QC measures indicated in 6.2, the following statement could be proven:

"On typical eyes and a reasonable shot, we can detect the apex of the cornea to within 68 microns 95% of the time ."

6.4 Recommendations for Further Tests and Improvements

6.4.1 Computation Reduction

To reduce the number of operations in the high resolution moving average step, we could limit evaluation to only those values between the indices indicated by edgeLeftLR and edgeRightLR. This was not done in the initial version because data outside these limits may be required in future tweaks of the algorithm.

This modification could save about 75% of the operations performed in this step.

6.4.2 Measurements to Limbus

Measurements to the limbus along the horizontal meridian may be possible since the rings are visible.

**DRAFT
E. SARVER**

6.4.3 Profile of Vertical Meridian

By tracing the vertical meridian additional information about the true shape of the cornea would be possible. This information could be used to augment the algorithm used to estimate the surface. In addition, it could be fit with a curve,( e.g. a conic, polynomial, or weighted sum of orthogonal basis functions such as the DCT), for studies, characterization of the cornea shape, or as a profile compression technique.

6.4.4 Improving Reliability of Algorithm

It cases where lashes occlude the center portion of the cornea, it will not be possible to use the current algorithm to detect the apex. It would be reasonable to include more than three rows from the temporal view array in the calculation of the apex. By including more information from this array, especially inferior (below) to the central row, we could increase the likelihood of detecting the rings in a non-occluded region of reflected rings.

6.5  Recommended Research and Publications

6.5.1 Accuracy Studies

Studies to determine accuracy and repeatability of apex detection for the following groups (each would be a separate study):

- Geriatric and /or pediatric patients
- Dry eye patients
- Post PRK and /or RK patients
- Post IOL patients
- Females with and without mascara

6.5.2 Cornea Shape Study

Use the true profile data to compute a parameter, such as eccentricity, for a large number of corneas. Report on the average eccentricity for various zones, patient populations, etc.

6.5.3 IR Illumination Study

Illuminate the cornea with IR, (possibly with rings removed), to evaluate the features which can be viewed from the side. Things to look for are:

DRAFT
E. SARVER

- Anatomical features such as cornea depth, entrance pupil diameter, etc.
- Artificial tear layer thickness and how it dries over time.
- Contact lens fits - with and without fluorescein

7.0 REFERENCES

[1] Margaret A. Ellis and Bjarne Stroustrup, The Annotated C++ Reference Manual (ANSI Base Document), Addison-Wesley Publishing Company, 1990.

[2] Foley, vanDam, Feiner, and Hughes, Computer Graphics Principles and Practice, Second Edition, Addison-Wesley Publishing Company, 1992.

[3] David J. Schanzlin and Jeffrey B. Robin, Corneal Topography - Measuring and Modifying the Cornea, Springer-Verlag, 1992.

[4] Alan Oppenheim and Ronald Schafer, Discrete-Time Signal Processing, Prentice Hall, 1989.

[5] Refael Gonzalez and Paul Wintz, Digital Image Processing, Addison-Wesley Publishing Company, 1990.

APPENDIX A: C++ FUNCTION LISTING

**DRAFT
E. SARVER**

FINDAPEX.H

```
/*
- - - - - - - - - - - - - - - - - - - - - - - - - - - - - - - - - - - - - - - - - - - - - - - - - - - - - - - - - - - - - - - - - - - - -
    File:
            findapex.h Purpose:
            Finds the apex of the side view of the cornea.

Author:
            Ed Sarver, Ph.D.
            Graphics and Image Processing Consultant
            18 Bogart Place
            Merritt Island, FL 32953
            (407) 453-3533

History:
            10/18/94: EJS Created.
- - - - - - - - - - - - - - - - - - - - - - - - - - - - - - - - - - - - - - - - - - - - - - - - - - - - - - - - - - - - - - - - - - - - -
*/
#define     NUM_COLS_SIDEVIEW   512     // number of columns in sideview image
#define     D_WIDTH             2       // half width of difference filter
#define     LR_WIDTH            20      // width of low res moving average
define     HR_WIDTH            4       // width of high res moving average typedef struct {
    double      diffBuffer[NUM_COLS_SIDEVIEW];
                                        // edge enhanced
    double      sumLRBuffer[NUM_COLS_SIDEVIEW];
                                        // low res moving sum
    double      sumHRBuffer[NUM_COLS_SIDEVIEW];
                                        // high res moving sum
    double      valueDiff;              // edge max value
    double      valueLR;                // low res max value
    double      valueHR;                // high res max value
    int         indexDiff;              // location of edge max value
    int         indexLR;                // location of low res max value
    int         indexHR;                // location of high res max value
    int         edgeRightLR;            // right edge of low res peak
    int         edgeRightHR;            // right edge of high res peak
    int         edgeLeftLR;             // left edge of low res peak
    int         edgeLeftHR;             // left edge of high res peak
} apexData;

typedef apexData far * LPAPEXDATA;

class CFindApex
{
public:
    CFindApex();
    ~CFindApex();

void        GetApex( unsigned char arr[NUM_COLS_SIDEVIEW], BOOL flagOD );

int         m_apex;                 // apex
    LPAPEXDATA  m_ap;

private:

void        ClearBuffers();
};
```

FINDAPEX.CPP

```
/*
-------------------------------------------------------------------------
    File:
            findapex.cpp Purpose:
            Finds the apex of the side view of the cornea.

Author:
            Ed Sarver, Ph.D.
            Graphics and Image Processing Consultant
            18 Bogart Place
            Merritt Island, FL 32953
            (407) 453-3533

History:
            10/18/94: EJS Created.
-------------------------------------------------------------------------
*/
#include "stdafx.h"
#include "math.h"
#include "findapex.h"

/*
-------------------------------------------------------------------------
 CFindApex constructor
-------------------------------------------------------------------------
*/
CFindApex::CFindApex()
{
    m_apex = 0;
    m_ap = new far apexData;
}

/*
-------------------------------------------------------------------------
 ~CFindApex descructor
-------------------------------------------------------------------------
*/
CFindApex::~CFindApex()
{ delete m_ap;

}

/*
-------------------------------------------------------------------------
 ClearBuffers Reset buffers to zero.
```

FINDAPEX.CPP

```cpp
*/
void CFindApex::ClearBuffers()
{
    int     i;

for (i=0; i<NUM_COLS_SIDEVIEW; i++) {
        m_ap->diffBuffer[i] = 0.;
        m_ap->sumLRBuffer[i] = 0.;
        m_ap->sumHRBuffer[i] = 0.;
    }

}

/*
 ----------------------------------------------------------------
 GetApex

Compute the location of the apex
 ----------------------------------------------------------------
*/
void CFindApex::GetApex(unsigned char imageBuff[NUM_COLS_SIDEVIEW], BOOL flagOD )
{ double      t;      // intermediate values stored here
    double      sum1;   // used for edge enhancement computation
    double      sum2;   // used for edge enhancement computation
    double      sum;    // used for moving average computation int         i,j;    // loop counters //  ---------- clear buffers ----------

ClearBuffers();

//  ---------- get edge enhancement -------------- m_ap->valueDiff = -1.;
    m_ap->indexDiff = 1;
    for (i=D_WIDTH; i<NUM_COLS_SIDEVIEW-D_WIDTH; i++) {
        sum1 = 0.;
        sum2 = 0.;
        for (j=1; j<=D_WIDTH; j++) {
            sum1 += (double) imageBuff[i+j];
            sum2 += (double) imageBuff[i-j];
        }
        t = sum1 - sum2;
        if (t<0.) t = -t;
        m_ap->diffBuffer[i] = t;
        if (t>m_ap->valueDiff) {
            m_ap->valueDiff = t;
            m_ap->indexDiff = i;
        }
    }
```

44

FINDAPEX.CPP

```
//  ---------- get low resolution moving average  ---------- sum = 0.;
    for (i=0; i<2*LR_WIDTH+1; i++)
        sum += m_ap->diffBuffer[i];

m_ap->valueLR = -1.;
    m_ap->indexLR = 1;
    for (i=LR_WIDTH; i<NUM_COLS_SIDEVIEW-(LR_WIDTH+1); i++) { m_ap->sumLRBuffer[i] = sum;
        if (sum > m_ap->valueLR) {
            m_ap->valueLR = sum;
            m_ap->indexLR = i;
        } sum += m_ap->diffBuffer[i+LR_WIDTH+1];
        sum -= m_ap->diffBuffer[i-LR_WIDTH];
    }

//  ---------- get left and right edge of low res array  ---------- t = m_ap->valueLR / 3.;

m_ap->edgeLeftLR = m_ap->indexLR;
    while ( m_ap->edgeLeftLR>LR_WIDTH &&
            m_ap->sumLRBuffer[m_ap->edgeLeftLR]>t ) { m_ap->edgeLeftLR--;

} m_ap->edgeRightLR = m_ap->indexLR;
    while ( m_ap->edgeRightLR<NUM_COLS_SIDEVIEW-LR_WIDTH &&
            m_ap->sumLRBuffer[m_ap->edgeRightLR]>t ) { m_ap->edgeRightLR++;

}

//  ---------- get high resolution moving average  ---------- sum = 0.;
    for (i=0; i<2*HR_WIDTH+1; i++)
        sum += m_ap->diffBuffer[i];

m_ap->valueHR = -1.;
    m_ap->indexHR = 1;
    for (i=HR_WIDTH; i<NUM_COLS_SIDEVIEW-(HR_WIDTH+1); i++) { m_ap->sumHRBuffer[i] = sum;
        if (sum > m_ap->valueHR) {
            m_ap->valueHR = sum;
            m_ap->indexHR = i;
        } sum += m_ap->diffBuffer[i+HR_WIDTH+1];
```

45

FINDAPEX.CPP

```
        sum -= m_ap->diffBuffer[i-HR_WIDTH];
    }

// ---------- get left and right edge from high resolution array ---------- t = m_ap->valueHR / 3.;

m_ap->edgeLeftHR = m_ap->edgeLeftLR;
    while ( m_ap->edgeLeftHR<m_ap->indexLR &&
            m_ap->sumHRBuffer[m_ap->edgeLeftHR]<t ) { m_ap->edgeLeftHR++;

} m_ap->edgeRightHR = m_ap->edgeRightLR;
    while ( m_ap->edgeRightHR>m_ap->indexLR &&
            m_ap->sumHRBuffer[m_ap->edgeRightHR]<t ) { m_ap->edgeRightHR--;

}

// ---------- save the desired edge in the apex ----- if (flagOD) {
        m_apex = m_ap->edgeRightHR;
    } else {
        m_apex = m_ap->edgeLeftHR;
    } return;
}
```

DRAFT
E. SARVER

APPENDIX B: DATA SHEET FOR ALGORITHM EVALUATION

SARVER.XLS

| PATIENT | FILE | MAX INT. | MAX ABS | MAX LOW | MAX HIGH | NOSE LOC | ERROR |
|---|---|---|---|---|---|---|---|
| 1 | 1 | 102 | 83 | 45 | 57 | 3 | 0 |
|  | 2 | 124 | 99 | 55 | 66 | 3 | 0 |
|  | 3 | 110 | 65 | 29 | 53 | 3 | -19 |
|  | 4 | 96 | 86 | 38 | 57 | 3 | 0 |
|  | 5 | 99 | 82 | 37 | 49 | 3 | 0 |
|  | 6 | 60 | 94 | 47 | 62 | 3 | 0 |
| 2 | 1 | 103 | 161 | 85 | 105 | 3 | 0 |
|  | 2 | 128 | 154 | 76 | 98 | 1.5 | 0 |
|  | 3 | 134 | 187 | 98 | 118 | 0.5 | 0 |
|  | 4 | 133 | 126 | 73 | 86 | 0 | 0 |
|  | 5 | 126 | 146 | 81 | 96 | 0 | -3 |
|  | 6 | 128 | 138 | 78 | 94 | 1 | 0 |
| 3 | 1 | 99 | 151 | 86 | 101 | 3 | 0 |
|  | 2 | 96 | 164 | 90 | 105 | 3 | 0 |
|  | 3 | 124 | 169 | 93 | 110 | 2 | 0 |
|  | 4 | 90 | 106 | 55 | 67 | 3 | 0 |
|  | 5 | 97 | 102 | 59 | 69 | 3 | 0 |
|  | 6 | 90 | 135 | 75 | 90 | 3 | 0 |
| 4 | 1 | 104 | 142 | 79 | 96 | 2.8 | 0 |
|  | 2 | 106 | 144 | 83 | 98 | 3 | 0 |
|  | 3 | 100 | 154 | 82 | 104 | 3 | 0 |
|  | 4 | 92 | 118 | 66 | 79 | 3 | 0 |
|  | 5 | 82 | 111 | 64 | 76 | 3 | 0 |
|  | 6 | 88 | 115 | 63 | 72 | 3 | 0 |
| 5 | 1 | 136 | 208 | 112 | 133 | 0 | 0 |
|  | 2 | 134 | 169 | 97 | 113 | 0.5 | 0 |
|  | 3 | 129 | 176 | 102 | 119 | 1 | 0 |
|  | 4 | 127 | 153 | 88 | 104 | 0.1 | -3 |
|  | 5 | 128 | 156 | 85 | 101 | 0 | -2 |
|  | 6 | 118 | 141 | 80 | 90 | 0 | -3 |
| 6 | 1 | 86 | 105 | 35 | 48 | 0 | 3 |
|  | 2 | 101 | 84 | 43 | 58 | 0 | 2 |
|  | 3 | 104 | 102 | 51 | 65 | 0 | 3 |
|  | 4 | 103 | 68 | 37 | 43 | 0 | -2 |
|  | 5 | 131 | 141 | 61 | 79 | 0 | -3 |
|  | 6 | 157 | 168 | 78 | 92 | 0 | 4 |
| 7 | 1 | 109 | 115 | 61 | 74 | 3 | 0 |
|  | 2 | 109 | 120 | 61 | 72 | 3 | 0 |
|  | 3 | 104 | 119 | 60 | 75 | 3 | 0 |
|  | 4 | 92 | 82 | 44 | 51 | 2.8 | 0 |
|  | 5 | 132 | 115 | 62 | 73 | 2 | 0 |
|  | 6 | 145 | 114 | 61 | 71 | 1 | -2 |
| 8 | 1 | 110 | 116 | 59 | 75 | 3 | 0 |
|  | 2 | 111 | 113 | 60 | 74 | 3 | 0 |
|  | 3 | 108 | 105 | 56 | 68 | 3 | 0 |
|  | 4 | 93 | 85 | 45 | 58 | 3 | 0 |
|  | 5 | 99 | 98 | 54 | 64 | 3 | 0 |

48

SARVER.XLS

|   |   |     |     |     |     |     |    |
|---|---|-----|-----|-----|-----|-----|----|
|   | 6 | 91  | 89  | 38  | 42  | 3   | 0  |
| 9 | 1 | 91  | 142 | 79  | 92  | 3   | 0  |
|   | 2 | 90  | 139 | 73  | 89  | 3   | 0  |
|   | 3 | 99  | 127 | 69  | 80  | 2   | 0  |
|   | 4 | 125 | 117 | 64  | 78  | 2   | 0  |
|   | 5 | 127 | 119 | 67  | 81  | 1   | 2  |
|   | 6 | 131 | 132 | 76  | 87  | 2   | -1 |
| 10| 1 | 115 | 188 | 101 | 123 | 3   | 0  |
|   | 2 | 116 | 197 | 101 | 122 | 3   | 0  |
|   | 3 | 106 | 164 | 95  | 116 | 3   | 0  |
|   | 4 | 115 | 144 | 83  | 98  | 2   | 0  |
|   | 5 | 93  | 109 | 64  | 73  | 2.8 | 0  |
|   | 6 | 101 | 116 | 70  | 84  | 2   | 0  |
| 11| 1 | 122 | 179 | 94  | 118 | 3   | 0  |
|   | 2 | 123 | 173 | 96  | 119 | 3   | 0  |
|   | 3 | 127 | 194 | 102 | 127 | 3   | 0  |
|   | 4 | 97  | 151 | 83  | 97  | 3   | 0  |
|   | 5 | 100 | 153 | 85  | 103 | 3   | 0  |
|   | 6 | 100 | 139 | 79  | 97  | 3   | 0  |
| 12| 1 | 91  | 92  | 42  | 58  | 2   | 0  |
|   | 2 | 107 | 155 | 76  | 94  | 2.8 | 0  |
|   | 3 | 128 | 127 | 68  | 83  | 2   | 0  |
|   | 4 | 79  | 84  | 45  | 54  | 3   | 0  |
|   | 5 | 107 | 120 | 62  | 77  | 2   | 0  |
|   | 6 | 107 | 112 | 58  | 70  | 2.8 | 0  |
| 13| 1 | 82  | 93  | 51  | 59  | 3   | 0  |
|   | 2 | 77  | 72  | 41  | 50  | 3   | 0  |
|   | 3 | 77  | 84  | 44  | 53  | 3   | 0  |
|   | 4 | 99  | 55  | 26  | 32  | 2   | 0  |
|   | 5 | 90  | 83  | 48  | 56  | 3   | 0  |
|   | 6 | 105 | 90  | 51  | 60  | 3   | 0  |
| 14| 1 | 106 | 90  | 45  | 62  | 2   | 0  |
|   | 2 | 99  | 86  | 45  | 56  | 2.8 | -5 |
|   | 3 | 89  | 65  | 37  | 46  | 2.8 | 0  |
|   | 4 | 99  | 98  | 45  | 61  | 3   | 0  |
|   | 5 | 99  | 101 | 49  | 63  | 3   | 0  |
|   | 6 | 94  | 89  | 45  | 55  | 3   | 0  |
| 15| 1 | 108 | 96  | 35  | 48  | 1   | 0  |
|   | 2 | 99  | 96  | 35  | 43  | 1   | 0  |
|   | 3 | 93  | 75  | 34  | 41  | 2   | 0  |
|   | 4 | 108 | 60  | 32  | 41  | 3   | 0  |
|   | 5 | 106 | 42  | 21  | 25  | 2.8 | -6 |
|   | 6 | 92  | 57  | 21  | 36  | 0   | -4 |
| 16| 1 | 101 | 133 | 70  | 84  | 3   | 0  |
|   | 2 | 99  | 154 | 87  | 104 | 3   | 0  |
|   | 3 | 103 | 175 | 86  | 108 | 3   | 0  |
|   | 4 | 135 | 158 | 82  | 95  | 0   | 0  |
|   | 5 | 144 | 186 | 92  | 106 | 0   | 3  |
|   | 6 | 136 | 159 | 88  | 103 | 0   | -2 |

49

SARVER.XLS

| | | | | | | | |
|---|---|---|---|---|---|---|---|
| 17 | 1 | 94 | 136 | 70 | 82 | 3 | 0 |
| | 2 | 114 | 143 | 77 | 92 | 3 | 0 |
| | 3 | 97 | 129 | 65 | 75 | 3 | 0 |
| | 4 | 114 | 81 | 43 | 56 | 3 | 0 |
| | 5 | 111 | 108 | 45 | 53 | 3 | 0 |
| | 6 | 102 | 123 | 61 | 72 | 3 | 0 |
| 18 | 1 | 129 | 111 | 59 | 74 | 0.5 | 0 |
| | 2 | 99 | 114 | 64 | 79 | 2 | 0 |
| | 3 | 125 | 126 | 66 | 80 | 0 | 3 |
| | 4 | 97 | 103 | 56 | 67 | 3 | 0 |
| | 5 | 128 | 113 | 60 | 69 | 2 | 0 |
| | 6 | 109 | 103 | 53 | 65 | 2 | 0 |
| 19 | 1 | 113 | 93 | 36 | 46 | 3 | 0 |
| | 2 | 146 | 157 | 83 | 100 | 2 | 0 |
| | 3 | 102 | 140 | 80 | 95 | 3 | 0 |
| | 4 | 89 | 40 | 19 | 23 | 0 | -9 |
| | 5 | 79 | 70 | 36 | 47 | 1 | 0 |
| | 6 | 85 | 81 | 38 | 52 | 1 | 0 |
| 20 | 1 | 102 | 86 | 50 | 61 | 3 | 0 |
| | 2 | 99 | 90 | 51 | 62 | 3 | 0 |
| | 3 | 94 | 100 | 56 | 70 | 3 | 0 |
| | 4 | 90 | 65 | 38 | 44 | 3 | 0 |
| | 5 | 86 | 72 | 33 | 41 | 3 | 0 |
| | 6 | 79 | 55 | 29 | 35 | 3 | 0 |
| MIN | | 60.0 | 40.0 | 19.0 | 23.0 | 0.0 | -19.0 |
| MAX | | 157.0 | 208.0 | 112.0 | 133.0 | 3.0 | 4.0 |
| MEAN | | 106.1 | 118.0 | 62.2 | 75.6 | 2.2 | -0.5 |
| SD | | 18.5 | 37.8 | 21.9 | 25.3 | 1.1 | 2.3 |

APPENDIX C: EYELASH MEASUREMENTS

DRAFT
E. SARVER

LASHES.XLS

| EYE LASHES MEASUREMENTS | | | | | | |
|---|---|---|---|---|---|---|
| | | POINT 1 | | POINT 2 | | |
| PATIENT | FILE | X | Y | X | Y | WIDTH |
| 1 | 1 | 165.0 | 61.0 | 174.0 | 73.0 | 15.0 |
| | 2 | 244.0 | 44.0 | 247.0 | 61.0 | 17.3 |
| | 3 | 326.0 | 59.0 | 332.0 | 72.0 | 14.3 |
| 3 | 4 | 343.0 | 60.0 | 347.0 | 49.0 | 11.7 |
| | 5 | 353.0 | 63.0 | 359.0 | 48.0 | 16.2 |
| 6 | 1 | 159.0 | 44.0 | 151.0 | 37.0 | 10.6 |
| | 1 | 199.0 | 58.0 | 205.0 | 65.0 | 9.2 |
| | 2 | 235.0 | 44.0 | 239.0 | 50.0 | 7.2 |
| | 3 | 257.0 | 59.0 | 263.0 | 65.0 | 8.5 |
| 12 | 1 | 291.0 | 45.0 | 281.0 | 36.0 | 13.5 |
| 14 | 1 | 284.0 | 47.0 | 277.0 | 31.0 | 17.5 |
| | 4 | 400.0 | 45.0 | 391.0 | 30.0 | 17.5 |
| | | 306.0 | 62.0 | 299.0 | 52.0 | 12.2 |
| MIN | | | | | | 7.2 |
| MAX | | | | | | 17.5 |
| MEAN | | | | | | 13.1 |
| STD | | | | | | 3.5 |

CONFIDENTIAL

MULTI-CAMERA CT (MCCT)

- Multiple camera corneal topography
- Advantages:
  - Auto-positioning, with verification
  - Curvature to limbus along horizontal meridian
  - True topography of vertical meridian
  - Method to correct for errors in positioning
  - Ability to provide automatic calibration
  - Big improvements at a small increase in cost of goods CONFIDENTIAL
1/10/94 page 1

The multi-camera corneal topography system is a major improvement in corneal topography. The basic idea is to view the cornea from the front and side (temporal) at the same time. This allows several advantages over conventional corneal topography.

Auto-positioning:

> The user positions the center of the rings using the usual front view. Image processing is used to determine the location of the apex in the side view. The difference between the desired and actual location is provided to the head positioning system automatically.

Curvature to limbus along horizontal meridian:

> The rings are captured in the side view as well as the front view. This allows curvature to be computed to the limbus along the horizontal meridian.

True topography of vertical meridian:

> The side view profile of the vertical meridian provides sagittal depth to about 15 micron resolution.

Method to correct for position errors:

> Using the side view, the true location of the apex can be determined. This location can be used to correct for position error.

Auto-calibration:

> Using the auto-positioning ability, calibration can be automated.

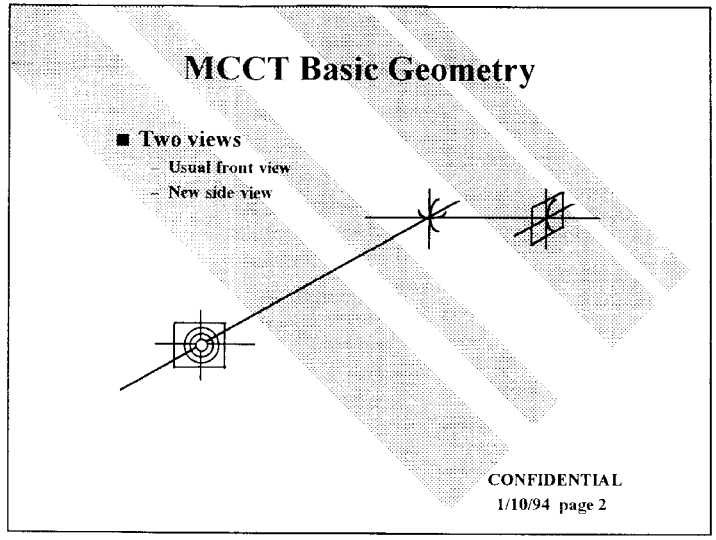

The basic geometry of the MCCT system allows for simultaneous views of the cornea at the same time.

Front view:

The front view provides the usual view of the reflected Placido rings.

Side (temporal) view:

The side view provides a profile of the cornea as well as a view of the reflected Placideo rings on the temporal hemisphere.

Note:

- The optical axis of each camera is aligned with the center of the acquired image and intersects at the desired location for the apex of the unit under test.

- The side view camera can be mounted so that it has a 90 bend where the existing focus aids are.

- The depth of view of the side view camera should be at least 6 mm.

- We may need a disposable on the bridge of the nose to provide a uiform background for the side view processing.

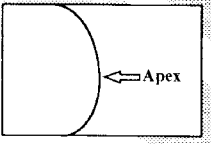

One of the major benefits of the MCCT is its ability to auto-position the z-axis location of the cornea. The optical axis of the side view should correspond to the apex of the cornea. The paradigm for auto-positioning is as follows:

User manually centers rings in front view:

> Using the joystick, the user manually centers the rings and provides some measure of focusing. The user then hits the acquisition signal.

A shot from the side view camera is processed:

> • Digitize image from the side view camera.
>
> • Find leading edge of cornea using matched filter, region of interest, and maximum operation.
>
> • Determine number of steps to move stepper in head unit and update position and take shot.
>
> • Matched filter impulse response should be:

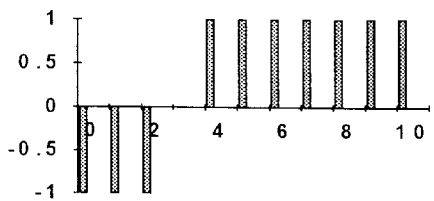

56

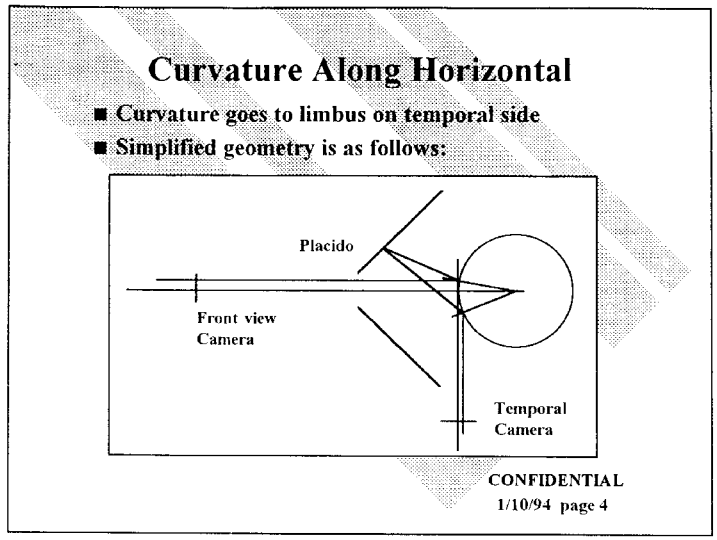

From the temporal (side view) camera, we are able to see the Placido rings reflected on the surface of the cornea.

Ra and Rt:

Using the delta algorithm, we can compute the instantaneous radius of curvature in the tangential plane (w.r.t. the front view camera). From this we can compute the axial radius, Ra.

Rs:

If we use the checkerboard Placido, we can compute the sagittal radius of curvature. This will employ some version of the delta algorithm.

Location of curvature w.r.t. front view:

The virtual image location will be used to determine the position of the curvature computed above.

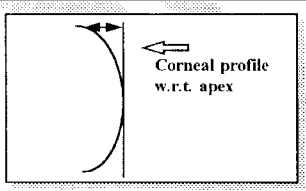

The temporal camera will allow us to determine the true profile of the vertical meridian. The exact range and resolution (accuracy) will depend upon the final magnification we choose.

Range and Resolution:

- Magnification should provide proper range and resolution of corneal profile, but must not be too sensitive as to make auto-positioning difficult. Note that higher resolution makes the peripheral curvature data more accurate.

Uses of profile data:

- May be useful in examining cornea for central islands.
- Will eliminate some of the assumptions associated with traditional corneal topography systems.
- May make contact lens fitting more exact (e.g. improve fl. sim.)
- Could provide data for conic fit.
- Market differentiation

Data obtained:

- Data obtained using matched filter as indicated in auto-positioning
- Data related to apex location (not assumed origin of coordinate system)
- Data stored in single array > CONFIDENTIAL
>
> ## POSITION ERROR CORRECTION
>
> - As with the previous position aids, the temporal shot can be stored with the exam file to verify a "proper" exam was taken.
> - By locating the apex (x and y in the image), we can correct for the position error of the shot.
>
> [Diagram: Correct position / Shifted "back" / Measure this distance]
>
> CONFIDENTIAL
> 1/10/94 page 6

The temporal shot can be saved with a superimposed "reference line" indicating the desired (or expected) apex location and the corneal apex as detected by the software. This will be helpful in verifying that the image processing was correct with respect to the assumed position of the apex. In addition, we can provide the following functions:

Reject if the image is out of focus:

By knowledge of the depth of field of the front view camera, we can use the measured apical distance to determine if the shot was out of focus. If is was, we can reject analysis.

Account for position error using analysis:

Using analysis such as that indicated in the diagram above, we can analytically account for position errors.

Account for position error using LUT's:

Another method to account for position errors is to extend the calibration concept to include calibration arrays for repositioned calibration spheres. Thus, we would look up the radius of curvature based upon the front image radial distance and theta, and the temporal image apex location.

AUTOMATIC CALIBRATION

- With a re-engineered calibration sphere holder and the temporal view, we can provide fully automatic calibration.
- This has several advantages:
  - Saves user time
  - More accurate
  - Market advantage Provides background for side shot.

With computer control of all three axes, we can automatically calibrate the system. The basic idea is as follows:

User places calibration spheres in holder and positions first ball:

The user would be responsible for placing a the calibration spheres in the chin rest and positioning the first sphere. The software would verify that this has been properly completed before proceeding.

Automatic processing:

- For each sphere the following is performed:

- Move the sphere to the desired apical position using the auto-position function.

- Take a shot and verifiy the rings are centered. Adjust x,y on the front image until the rings are centered.

- Take the shots and store results.

- Move the sphere to a desired apical position in front of the nominal apical position and repeat the calibration.

- Move the sphere to a desired apical position in back of the nominal apical position and repeat the calibration.

CONFIDENTIAL

SMALL COGS INCREASE

- In brute force implementation we add:
  - 2 Cameras
  - Cables for cameras and stepper control
  - Different optics and fixtures
  - New Calibration assembly
- Use same frame grabber board
- Eliminate old position aids CONFIDENTIAL
1/10/94 page 8

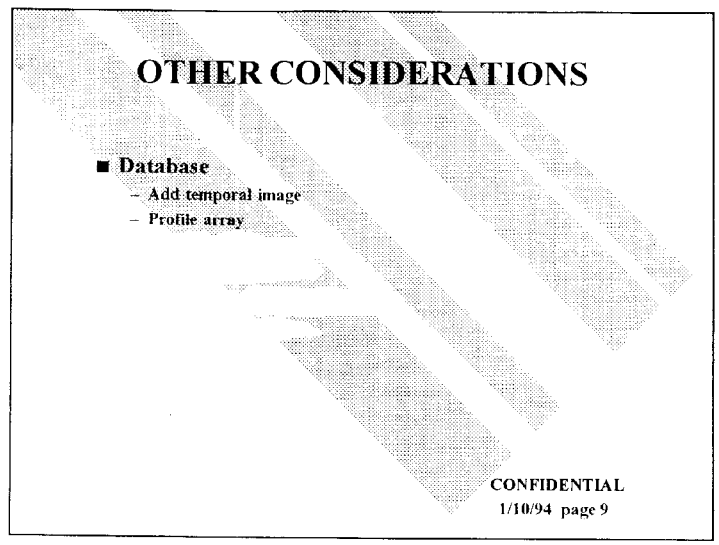

MULTI-CAMERA CORNEAL TOPOGRAPHY
CORNEAL APEX LOCATION ALGORITHM

ED SARVER

1.0 PURPOSE

The purpose of this document is to provide details of the corneal apex location algorithm for the multi-camera corneal topography system.

2.0 COORDINATE SYSTEM AND DEFINITIONS

The temporal view of the OS cornea is illustrated in Figure 1.

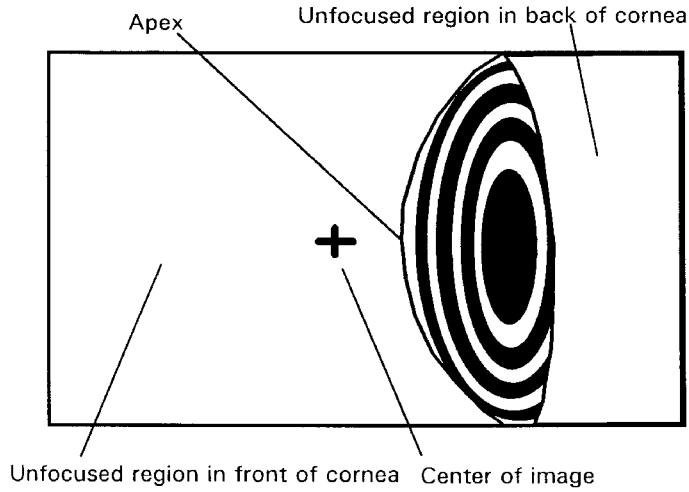

FIGURE 1.

We will refer to the unfocused region in front of the cornea as region A; the focused region of reflected rings on the cornea as region B; and the unfocused region in back of the cornea as region C. Our goal will be to determine the location of the apex with respect to the center of the image. We will refer to a "profile" as the sequence of intensity values for a given row of the image.

3.0 EXAMPLE PROFILES

The profile for a calibration sphere with no background is shown in Figure 2.

In this figure, the regions are approximately as follows:

| Regions for Cal Profile | | |
|---|---|---|
| Region | Start | Stop |
| A | 0 | 264 |
| B | 265 | 352 |
| C | 353 | 512 |

If we apply the simple zero-phase high-pass filter defined by the following:

$$y[n] = \left| \sum_{k=-2}^{2} x[n-k] h[k] \right|$$

where $$h[k] = \{-1,-1,0,1,1\}$$

Then we have the profile of Figure 3.

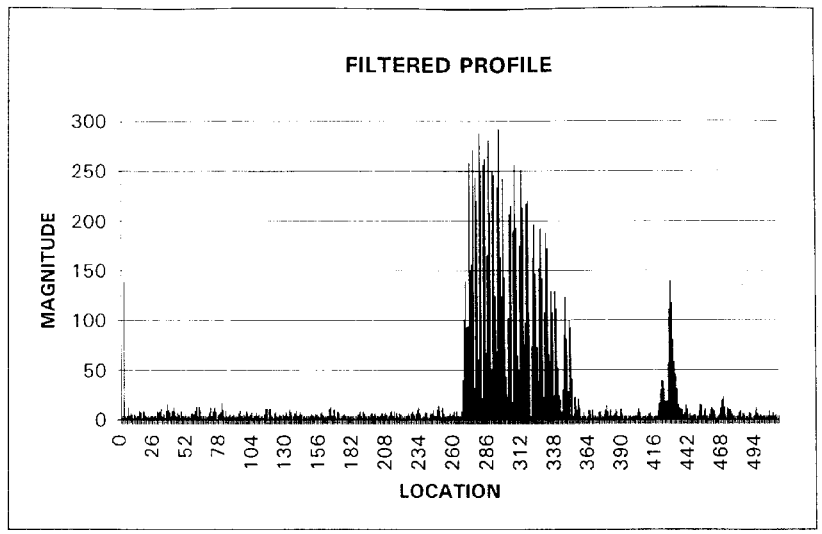
FIGURE 3.
The corresponding profiles for a "dark iris" eye and a "light iris" eye are provided in Figures 4 & 5 and Figures 6 & 7, respectively.
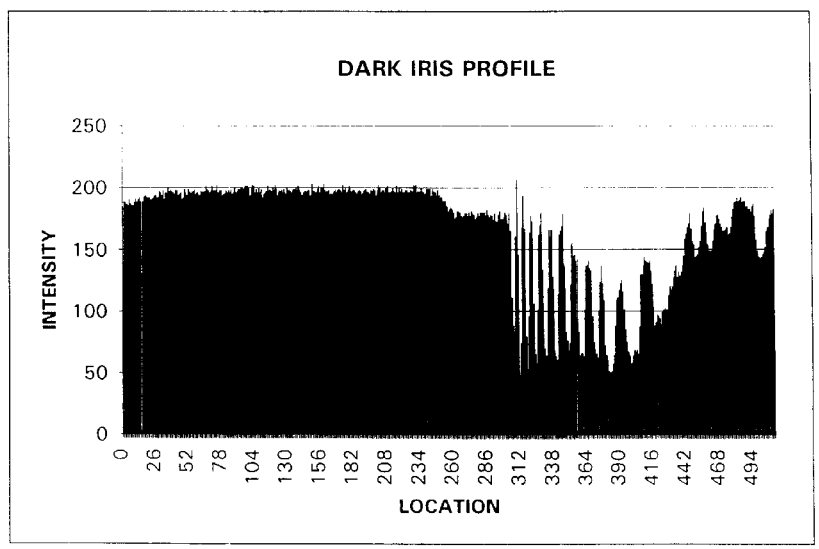

FIGURE 4.
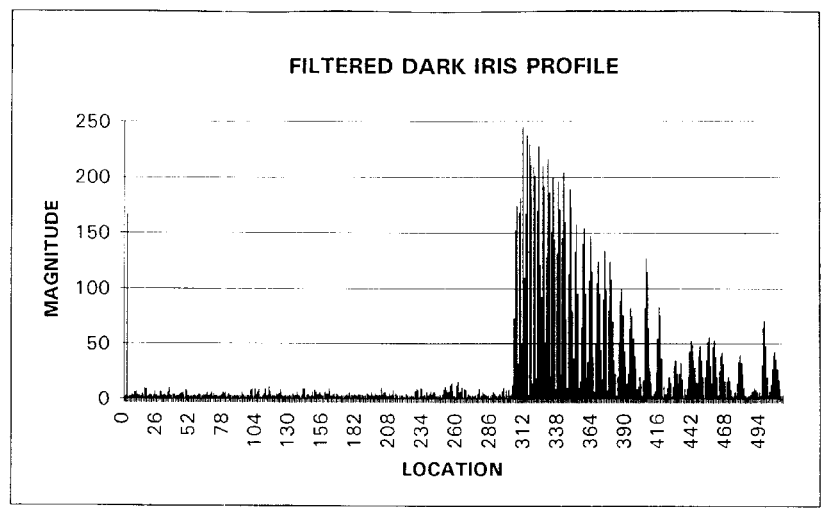
FIGURE 5.
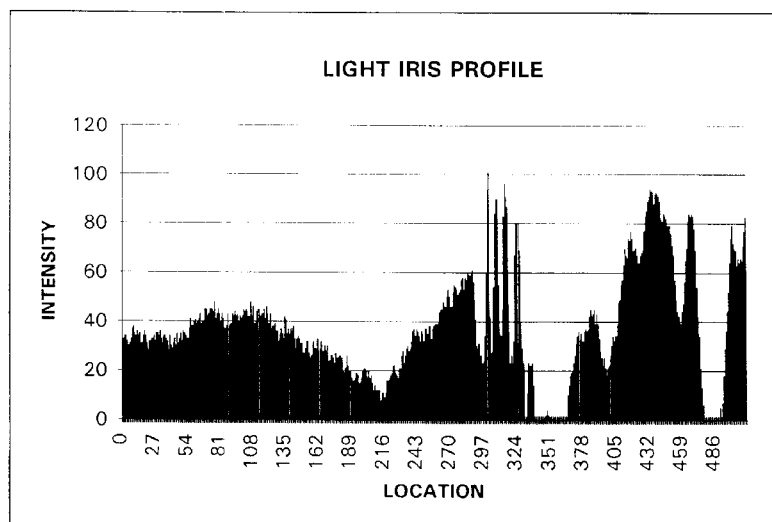
FIGURE 6.

| FOR DARK IRIS PROFILE | | | | | | |
|---|---|---|---|---|---|---|
| LOCATION | INTENSITY | DISTANCE | MEAN | STD. DEV | H1 | H2 |
| 290 | 177 | -1.03324 | 4.92 | 3.79389 | 1 | 4 |
| 291 | 174 | -0.485449 | 4.86 | 3.831501 | 3 | 4 |
| 292 | 179 | 0.052129 | 4.8 | 3.836665 | 5 | 4 |
| 293 | 173 | -0.725288 | 4.78 | 3.832962 | 2 | 4 |
| 294 | 173 | 0.579186 | 4.78 | 3.832962 | 7 | 4 |
| 295 | 178 | 1.339788 | 4.9 | 3.806573 | 10 | 4 |
| 296 | 181 | -1.054763 | 5.06 | 3.849208 | 1 | 4 |
| 297 | 175 | 0.771517 | 5 | 3.888444 | 8 | 5 |
| 298 | 175 | -1.328898 | 5.14 | 3.867868 | 0 | 11 |
| 299 | 176 | 0.747813 | 5.06 | 3.931463 | 8 | 25 |
| 300 | 180 | -0.778336 | 5.06 | 3.931463 | 2 | 40 |
| 301 | 178 | 0.031082 | 4.88 | 3.860777 | 5 | 42 |
| 302 | 171 | 2.132958 | 4.82 | 3.835049 | 13 | 57 |
| 303 | 180 | 17.010851 | 4.96 | 3.9998 | 73 | 73 |
| 304 | 165 | 14.103004 | 6.28 | 10.332551 | 152 | 78 |
| 305 | 111 | 7.211768 | 9.08 | 22.868179 | 174 | 99 |
| 306 | 88 | 0.606783 | 12.28 | 32.499255 | 32 | 109 |
| 307 | 83 | 4.760428 | 12.78 | 32.606312 | 168 | 124 |
| 308 | 161 | 4.213717 | 16.12 | 39.129344 | 181 | 144 |
| 309 | 206 | 0.667589 | 19.72 | 45.357266 | 50 | 138 |
| 310 | 146 | 4.930221 | 20.48 | 45.539539 | 245 | 145 |

| DATA FOR CAL PROFILE | | | | | | |
|---|---|---|---|---|---|---|
| LOCATION | INTENSITY | DISTANCE | MEAN | STD. DEV. | H1 | H2 |
| 260 | 169 | -0.601312 | 5.06 | 3.425843 | 3 | 4 |
| 261 | 174 | 0.881415 | 4.98 | 3.42631 | 8 | 7 |
| 262 | 175 | -1.162776 | 4.96 | 3.405642 | 1 | 16 |
| 263 | 172 | -0.551014 | 4.9 | 3.448188 | 3 | 28 |
| 264 | 172 | -0.816497 | 4.8 | 3.429286 | 2 | 36 |
| 265 | 174 | 0.932571 | 4.82 | 3.409927 | 8 | 44 |
| 266 | 171 | 10.264042 | 4.84 | 3.425551 | 40 | 67 |
| 267 | 165 | 15.660292 | 5.62 | 5.962852 | 99 | 80 |
| 268 | 141 | 9.222153 | 7.48 | 14.369746 | 140 | 94 |
| 269 | 105 | 3.53047 | 10.18 | 23.458636 | 93 | 119 |
| 270 | 91 | 3.138211 | 12.02 | 26.123162 | 94 | 121 |
| 271 | 122 | 8.5725 | 13.88 | 28.477107 | 258 | 143 |
| 272 | 218 | 2.948803 | 19.04 | 44.411242 | 150 | 159 |
| 273 | 236 | 2.793689 | 22.02 | 47.958103 | 156 | 156 |
| 274 | 127 | 4.783651 | 25.06 | 51.412609 | 271 | 169 |
| 275 | 57 | 0.026543 | 30.36 | 61.786976 | 32 | 183 |
| 276 | 126 | 3.439392 | 30.98 | 61.644623 | 243 | 177 |
| 277 | 205 | 2.698307 | 35.72 | 68.294667 | 220 | 177 |
| 278 | 222 | 0.288734 | 39.96 | 72.869736 | 61 | 187 |
| 279 | 181 | 3.3939 | 41.08 | 72.754062 | 288 | 179 |
| 280 | 89 | 2.51793 | 46.82 | 80.296124 | 249 | 169 |

| DATA FOR LIGHT IRIS PROFILE | | | | | | |
|---|---|---|---|---|---|---|
| LOCATION | INTENSITY | DISTANCE | MEAN | STD. DEV. | H1 | H2 |
| 280 | 58 | -1.091603 | 5.58 | 4.195664 | 1 | 4 |
| 281 | 53 | -1.285979 | 5.42 | 4.214689 | 0 | 4 |
| 282 | 58 | 0.145668 | 5.38 | 4.256242 | 6 | 4 |
| 283 | 57 | 0.598482 | 5.48 | 4.210653 | 8 | 5 |
| 284 | 60 | -0.588982 | 5.48 | 4.210653 | 3 | 9 |
| 285 | 59 | -0.801127 | 5.36 | 4.194091 | 2 | 13 |
| 286 | 59 | -0.801127 | 5.36 | 4.194091 | 2 | 17 |
| 287 | 60 | -1.039558 | 5.36 | 4.194091 | 1 | 18 |
| 288 | 61 | 4.019876 | 5.18 | 4.184208 | 22 | 18 |
| 289 | 56 | 9.798768 | 5.3 | 4.561798 | 50 | 18 |
| 290 | 41 | 6.717638 | 6.1 | 7.72593 | 58 | 19 |
| 291 | 30 | 2.813826 | 7.2 | 10.590562 | 37 | 19 |
| 292 | 29 | 0.534931 | 7.94 | 11.328566 | 14 | 23 |
| 293 | 31 | -0.106049 | 8.2 | 11.315476 | 7 | 33 |
| 294 | 26 | 0.244083 | 8.24 | 11.307626 | 11 | 43 |
| 295 | 26 | 0.145076 | 8.36 | 11.304442 | 10 | 43 |
| 296 | 23 | -0.22563 | 8.54 | 11.257371 | 6 | 46 |
| 297 | 24 | 3.242935 | 8.64 | 11.212065 | 45 | 55 |
| 298 | 34 | 7.953654 | 9.52 | 12.256003 | 107 | 59 |
| 299 | 60 | 6.850516 | 11.6 | 18.305191 | 137 | 65 |
| 300 | 94 | 1.372143 | 14.24 | 25.332635 |  | 75 |

74

4.0 ALGORITHM

The strategy (for processing a right eye) indicated in section 3.0 can be stated as follows. For the central row, x[n], compute the "high-passed" sequence y[n]. Starting from the "left" at k = N+1. Compute the mean and standard deviation for a neighborhood (from k-N-1 to k-1) for the y[n] sequence. Determine "how far" y[k] is from the mean just computed. If it exceeds 5 standard deviations, we will say it does not belong to the distribution which characterizes the A region, so it must belong to the B region. If it does not exceed 5 standard deviations, we continue to the "right" looking for the first sample which does not fit in the distribution. The steps are as follows:

| 1. | Compute y[n] |
|---|---|
| | set W = 2<br>set NUM_COLS = 512<br>set y[n] = 0 for all n<br><br>for n=W to NUM_COLS {<br>    sum_1 = 0<br>    sum_2 = 0<br>    for k=1 to W {<br>        sum_1 = sum_1 + x[n+k]<br>        sum_2 = sum_2 - x[n-k]<br>    }<br>    y[n] = abs( sum_1 - sum_2 )<br>} |

| 2. | Scan for outlier |
|---|---|
| | init sum, sum_sq<br><br>for n=N+1 to NUM_COLS do the following<br>    y_new = y[n]<br>    y_old = y[n-(N+1)]<br>    sum = sum + y_new - y_old<br>    sum_sq = sum_sq + y_new*y_new - y_old*y_old<br>    mean = sum / num<br>    var = (sum_sq / num) - mean*mean<br>    sd = sqrt(var)<br>    t = (y[n] - mean) / sd<br>    if (t>5) then do the following<br>        y[n] is in region B, this is the boundary<br>        done |

5.0 CONSISTENCY CHECK FOR COMPUTATION

The algorithm in section 4.0 will find a "resonable" apex for a temporal image profile. We would like to determine if this solution is consistent with what we would normally expect. We note the following for "typical" profiles (y[n] is high-pass filtered region A window):

1. Mean of y[n] is "small"
2. Standard deviation of y[n] is "small"
3. Difference of apex y[n] to mean is "large"
4. The maximum of the smoothed y[n] is "near" the apex
5. The width of the ring area is "medium"
6. The maximum of the smoothed y[n] is "large"

These descriptions are to be "anded" together, so that we expect the profile have a small mean and a small standard deviation and ... . To evaluate these imprecise statements, we will use fuzzy sets. The membership functions for each of the above rules are provided next.

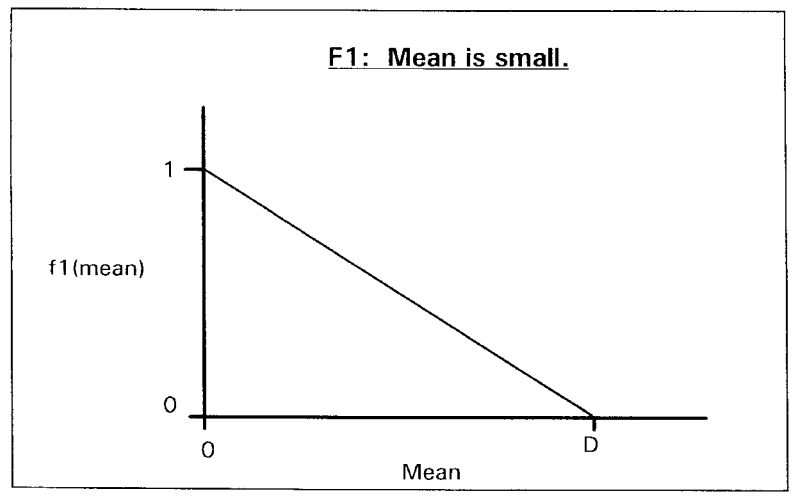

FIGURE 20.

$$f = \begin{cases} \dfrac{x-A}{B-A} & \text{for } A \le x < B \\ 1 & \text{for } B \le x < C \\ 1 - \dfrac{x-C}{D-C} & \text{for } C \le x < D \\ 0 & \text{for all other } x \end{cases}$$

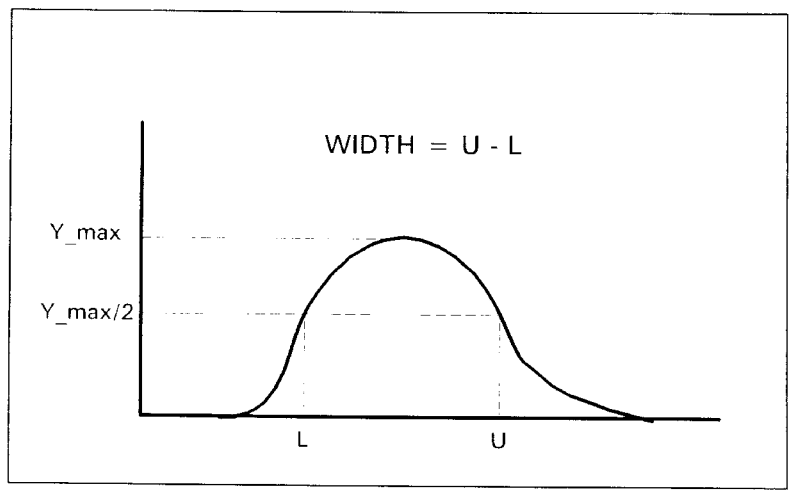

FIGURE 25.

Intersection of the fuzzy sets:

To consider all five fuzzy rules at once, we will use the traditional MIN operation to compute the intersection. Thus, the final fuzzy membership value to the set of "consistent" images is:

$$f(x_1, x_2, x_3, x_4, x_5, x_6) = \min\{f_i(x_i) \forall i \in (1,\ldots,6)\}$$

Parameter values for the fuzzy membership functions are:

| Parameters for Trapezoidal Functions | | | | | |
|---|---|---|---|---|---|
| f(x) | Description | A | B | C | D |
| 1 | Mean is small | 0 | 0 | 10 | 20 |
| 2 | SD is small | 0 | 0 | 5 | 6 |
| 3 | Diff. is large | 5 | 6 | INF | INF |
| 4 | Max. is near apex | 20 | 30 | 70 | 80 |
| 5 | Width is medium | 30 | 40 | 90 | 100 |
| 6 | Max. is large | 40 | 50 | INF | INF |

Using these parameters, the three profiles from the examples section have following fuzzy membership values:

| Parameter Values | | | |
|---|---|---|---|
| Parameter | Cal | Dark Iris | Light Iris |
| x1 | 4.84 | 4.96 | 5.30 |
| x2 | 3.43 | 4.00 | 4.56 |
| x3 | 10.26 | 17.01 | 9.80 |
| x4 | 51.00 | 50.00 | 49.00 |
| x5 | 72.00 | 75.00 | 54.00 |
| x6 | 163.00 | 133.00 | 60.00 |

| Membership Values | | | |
|---|---|---|---|
| Set | Cal | Dark Iris | Light Iris |
| f1 | 1.00 | 1.00 | 1.00 |
| f2 | 1.00 | 1.00 | 1.00 |
| f3 | 1.00 | 1.00 | 1.00 |
| f4 | 1.00 | 1.00 | 1.00 |
| f5 | 1.00 | 1.00 | 1.00 |
| f6 | 1.00 | 1.00 | 1.00 |
| (1,2,3,4,5,6) | 1.00 | 1.00 | 1.00 |

Thus, we will say that the image is consistent if the final membership value is greater than:

MIN MEMBERSHIP VALUE: 0.8

81

| | |
|---|---|
| Filename: | MCCT_1.DOC |
| Directory: | K:\E_SARVER\DERIVE |
| Template: | H:\WINWORD\NORMAL.DOT |
| Title: | |
| Author: | Ed Sarver |
| Subject: | |
| Keywords: | |
| Comments: | |
| Create Date: | 3/28/94 12:10 PM |
| Revision Number: | 37 |
| Last Saved Date: | 4/12/94 1:28 PM |
| Last Saved By: | Ray Applegate |
| Total Editing Time: | 1 135 Minutes |
| Last Printed: | 6/28/94 3:31 PM |
| As of Last Complete Printing | |
|    Number of Pages: | 19 |
|    Number of Words: | 728 |
|    Number of Characters: | 5,772 |

MULTI-CAMERA SYSTEM
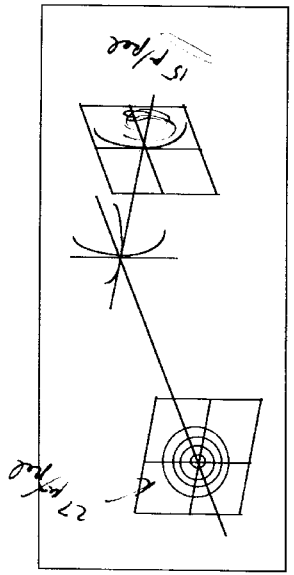
- Two views
  - Usual front view, new side (temporal) view
- Advantages
  - Auto-positioning, with verification
  - True topography of vertical meridian
  - Method to correct for errors in positioning
  - Automatic calibration
*EyeSys* TECHNOLOGIES

MCCT HARDWARE PROTOTYPE

- Video mux for OS/OD temporal camera
- Two frame grabbers in PC, controller card
- Position encoder for OS, OD, center
- Advanced head design
- Docking configuration
- ON/OFF switches under software control
  - Cameras
  - Main lamp

*EyeSys* TECHNOLOGIES

MCCT PROTOTYPE SOFTWARE

- Hardware control
- Advanced image processing
  - Apex detection
  - Fuzzy acceptance criteria
  - User verify and edit facility
- Auto-calibration
- Save temporal view for verification and future enhancements
- Auto-position test bed

*EyeSys* TECHNOLOGIES

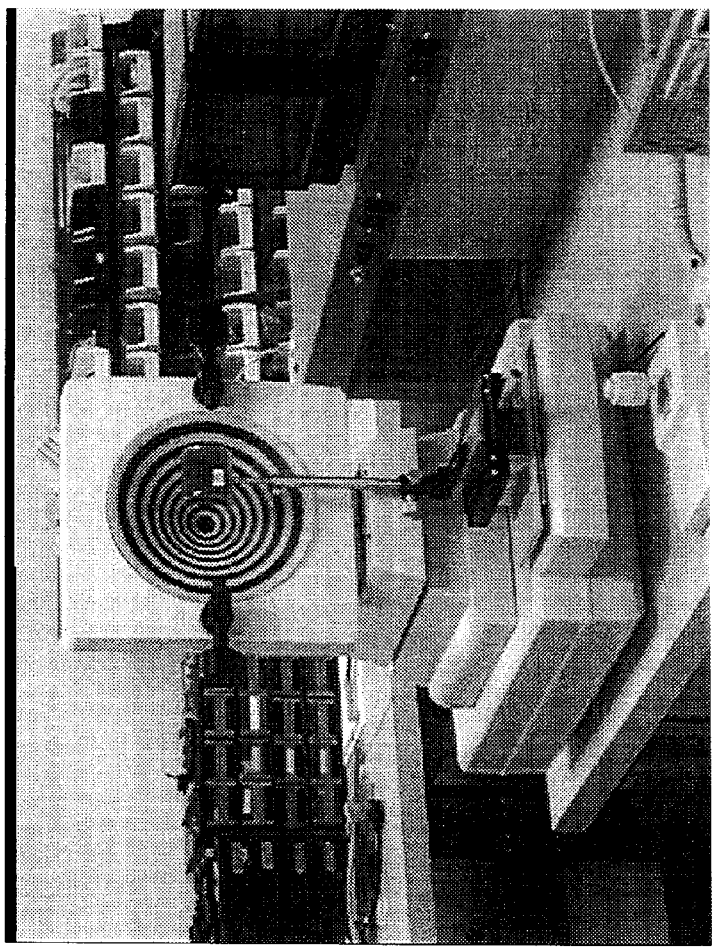

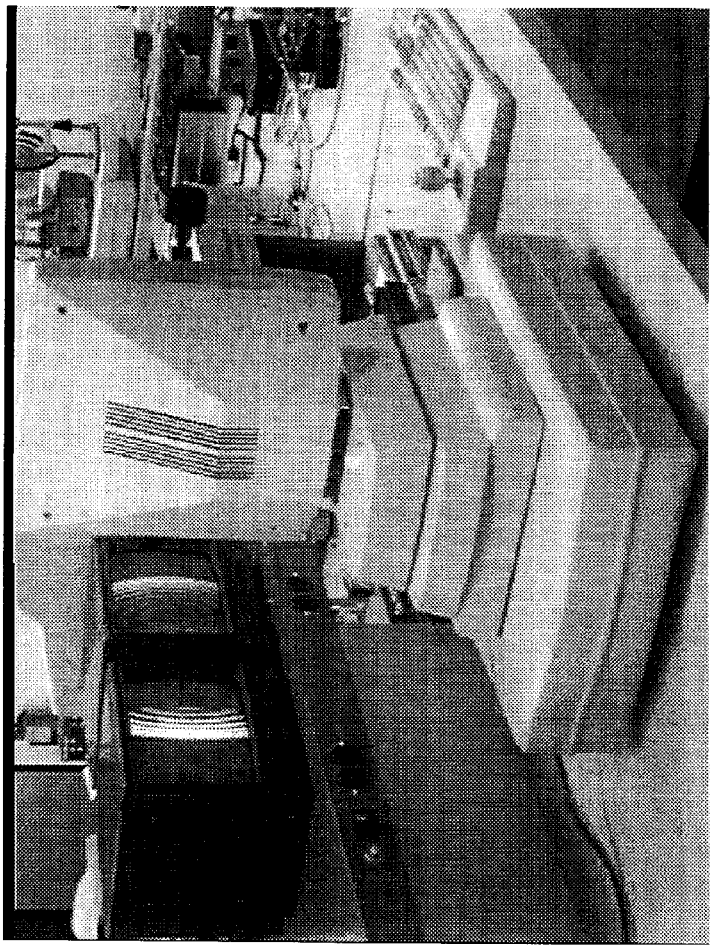

88

What is claimed:

1. An improvement upon apparatus for measuring a radius of curvature of a human cornea, said cornea having an apex, said apparatus including (A) means for reflecting an image on said cornea, (B) a front-view camera subsystem having an optical axis and a field of view that includes said cornea, said front-view camera subsystem including means for generating a digitized representation of said image, and (C) a processor subsystem programmed to process said digitized representation to produce an estimate of said radius of curvature; the improvement comprising:

(a) a first side-view camera subsystem:
      (1) having a field of view that includes said cornea,
      (2) including means for generating a digitized representation of said image,
      (3) being rigidly positioned relative to said front-view camera subsystem, and
      (4) having an optical axis that is substantially orthogonal to the optical axis of said front-view camera subsystem;
   (b) the optical axes of said front-view camera subsystem and of said first side-view camera subsystem collectively defining a coordinate system having an origin defined by the intersection of those optical axes;
   (c) a processor subsystem programmed:
      (1) to analyze said digitized representations generated by said front-view camera subsystem and said first side-view camera subsystem and to generate an error signal representing a displacement of said apex relative to said origin, and
      (2) to generate a positional signal representative of the position of said apex relative to said coordinate system; and
   (d) means to generate a periodically-updated visual display of said positional signal.

2. An apparatus for topographically mapping a reflecting surface, said reflecting surface having an apex, comprising:

(a) means for reflecting an image on said reflecting surface;
   (b) a front-view camera subsystem having an optical axis and a front field of view that includes said reflecting surface, said front-view camera subsystem including means for generating a first digitized representation of said image;
   (c) a first processor subsystem programmed to process said first digitized representation to produce topographic data of said reflecting surface, including estimates of radii of curvature of said reflecting surface at a plurality of points;
   (d) a first side-view camera subsystem having:
      (1) a field of view that includes a first side view of said reflecting surface,
      (2) means for generating a second digitized representation of said image, and
      (3) an optical axis that is substantially orthogonal to the optical axis of said front-view camera subsystem;
   (e) the respective optical axes of said front-view camera subsystem and said first side view camera subsystem collectively defining a coordinate system having an origin;
   (f) said first side-view camera subsystem and said front-view camera subsystem collectively comprising a camera assembly; and
   (g) a second processor subsystem programmed to analyze said digitized representations generated by said front-view camera subsystem and said first side-view camera subsystem and to generate an error signal representing a displacement of said apex relative to said origin.

3. The apparatus of claim 2, wherein said origin of the coordinate system is defined by the intersection of said optical axes.

4. The apparatus of claim 2, wherein said reflecting surface is a human cornea.

5. The invention of claim 2, wherein said reflecting surface is a contact lens.

6. The apparatus of claim 2 wherein said first side-view camera subsystem is rigidly positioned relative to said front-view camera subsystem.

7. The invention of claim 2, further comprising a closed-loop electromechanical positioning system responsive to said error signal for positioning said camera assembly so that the origin of said coordinate system is at the apex of said reflecting surface.

8. The invention of claim 2, wherein said second processor subsystem is programmed to generate and store in memory a positional signal representative of the position of said apex relative to said coordinate system.

9. The invention of claim 8, wherein said processor system generates a visual display of said positional signal.

10. The invention of claim 9, wherein said processor system is programmed to periodically update said visual display.

11. The invention of claim 2, wherein said camera assembly further comprises a second side-view camera subsystem rigidly positioned relative to said front-view camera subsystem and said first side-view camera subsystem having:

(1) a field of view that includes a second side-view of said reflecting surface opposite said first side view,
   (2) means for generating a third digitized representation of said image, and
   (3) an optical axis that is substantially orthogonal to the optical axis of said front-view camera subsystem.

12. The apparatus of claim 11, wherein said second side-view camera has an optical axis that lies in the plane that contains the optical axis of said first side-view camera.

13. The apparatus of claim 12, wherein the optical axis of said second side-view camera is parallel to the optical axis of the first side-view camera.

14. The invention of claim 2, wherein said second processor subsystem is programmed to process said error signal to generate a correction to said estimates of the radii of curvature.

15. The apparatus of claim 2, wherein the displacement of said apex that is represented by said error signal comprises a displacement along the optical axis of said front-view camera subsystem.

16. A keratometric apparatus for topographically analyzing a reflecting surface, comprising:

(a) means for reflecting an image off said reflecting surface;
   (b) a front-view camera for generating a first digitized signal representing a front view of said image;
   (c) a side-view camera for generating a second digitized signal representing a side-view of said image; and
   (d) a processor subsystem for receiving said front-view digitized signal and said side-view digitized signal and processing said signals for repeatably positioning said front-view camera and said side-view camera in relation to said reflecting surface and to estimate the radii of curvature at multiple points on said reflecting surface.

17. A method of finding the apex of a reflecting surface in a multi-camera corneal analysis system having a camera assembly including a side-view camera and a front-view camera comprising:

(a) using said side-view camera to capture a side-view image of said reflecting surface; and (b) determining an actual apex location by detecting a leading edge of said side-view image.

18. The method of claim 17 further comprising:

(a) determining a desired apex location; and (b) generating an error signal representing a difference between said actual location and said desired location.

19. The method of claim 17, further comprising displaying a representation of said error signal.

20. The method of claim 17, further comprising printing a representation of said error signal.

21. The method of claim 17, further comprising using said error signal to drive an electromechanical positioning system for positioning said camera assembly so that said actual apex is located at said desired location.

22. The method of claim 17, further comprising using said error signal to correct a radius of curvature measurement of the reflecting surface.

23. A method of automatically calibrating a multi-camera corneal analysis system having a camera assembly including a front-view camera and a side-view camera, comprising:

(a) using said side-view camera to detect an actual Z-axis location of an apex of a reflecting surface on a cornea with respect to a desired location of said apex;

(b) using said front-view camera to detect an actual X-axis and Y- axis location of said apex with respect to said desired location of said apex; and (c) generating an error signal for each axis, X, Y and Z, said error signals defined by a difference between said actual location and said desired location.

24. The method of claim 23, further comprising:

using at least one of said error signals to drive an electromechanical positioning system for positioning said camera assembly so that said apex is located at said desired location.

25. A keratometric apparatus for examining the cornea of an eye by means of a reflected image on the cornea of an illuminated target, said apparatus comprising:

a first camera positioned with its optical axis aligned with the optical axis of the eye to capture a front view of the cornea and the reflected image; and a second camera positioned on one side of the cornea, with the optical axis of the second camera intersecting the optical axis of the first camera substantially orthogonally, to capture a profile view of the cornea and said reflected image.

26. The apparatus of claim 25 wherein the optical axes of the two cameras intersect at an angle between about 75 and about 100 degrees.

27. The apparatus of claim 25 wherein the optical axes of the two cameras intersect at an angle between about 85 and about 95 degrees.

28. The apparatus of claim 25 wherein the optical axes of the two cameras intersect at an angle of about 90 degrees.

29. The apparatus of claim 25 wherein the target comprises a placido disk whose surface comprises a plurality of concentric rings with adjacent rings having different colors.

30. The apparatus of claim 25 wherein the target is stationary.

31. A keratometric method for examining an eye which includes forming a reflected image of an illuminated target on the cornea of the eye, said method comprising:

capturing a front view of the cornea and said image on a first camera whose optical axis is aligned with the optical axis of the eye; and capturing a side view of the cornea and said image on a second camera which is positioned to one side of the cornea and whose optical axis is substantially orthogonal to said optical axis of said first camera.

32. The method of claim 31 which further comprises detecting the actual apex of the cornea in said side view.

* * * * *